US008551729B2

(12) United States Patent
Deutscher et al.

(10) Patent No.: US 8,551,729 B2
(45) Date of Patent: Oct. 8, 2013

(54) **MUTANTS OF *LACTOBACILLUS CASEI* DEFECTIVE IN CARBON CATABOLISM REGULATION**

(75) Inventors: Josef Deutscher, Fontenay le Fleury (FR); Gaspar Perez Martinez, Valencia (ES); Vicente Monedero Garcia, Valencia (ES); Rosa Viana Ballester, Valencia (ES); Laurent Benbadis, Toulouse (FR); Anne Pierson, Fontenay-aux-Roses (FR); Jean-Michel Faurie, Jouy-en-Josas (FR)

(73) Assignees: Centre National de la Recherche Scientifique, Paris (FR); Consejo Superior de Investigaciones Cientificas, Madrid (ES); Compagnie Gervais Danone, Levallois-perret (FR)

( * ) Notice: Subject to any disclaimer, the term of this patent is extended or adjusted under 35 U.S.C. 154(b) by 1075 days.

(21) Appl. No.: 12/414,246

(22) Filed: Mar. 30, 2009

(65) Prior Publication Data

US 2011/0212223 A1    Sep. 1, 2011

Related U.S. Application Data

(62) Division of application No. 10/240,280, filed as application No. PCT/EP01/03951 on Mar. 30, 2001, now abandoned.

(30) Foreign Application Priority Data

Mar. 31, 2000    (EP) ................................ 00400894

(51) Int. Cl.
*A23C 9/12*    (2006.01)
*C12N 1/21*    (2006.01)

(52) U.S. Cl.
USPC ........................................ 435/39; 435/252.9

(58) Field of Classification Search
None
See application file for complete search history.

(56) References Cited

PUBLICATIONS

Viana et al. (Mol. Microbiol., 36:570-584, May 2000).*
Leloup et al. (Appl. Environ. Microbiol., 63:2117-2123, 1997).*
Yebra et al. (J. Bacteriol., 182:155-163, Jan. 2000).*

* cited by examiner

*Primary Examiner* — Brian J Gangle
(74) *Attorney, Agent, or Firm* — Oblon, Spivak, McClelland, Maier & Neustadt, L.L.P.

(57) ABSTRACT

The invention relates to the use of mutants of *L. casei* having at least a mutation impairing the regulation of a carbon catabolite repression (CCR) mechanism involving the PTS protein HPr, for the preparation of a food product.
The use of said mutants allows for instance to impart to said food products an improved texture and flavor, and/or a higher content in aroma compounds.

7 Claims, 9 Drawing Sheets

1st recombination

2nd recombination

SEQUENCE LISTING

```
<160> NUMBER OF SEQ ID NOS: 21

<210> SEQ ID NO 1
<211> LENGTH: 4150
<212> TYPE: DNA
<213> ORGANISM: Lactobacillus casei
<220> FEATURE:
<221> NAME/KEY: CDS
<222> LOCATION: (273)..(536)
<220> FEATURE:
<221> NAME/KEY: CDS
<222> LOCATION: (539)..(2263)

<400> SEQUENCE: 1
gtgacgccag aaacgttcat ggcgtttcgc gcggcatgga cgaattatcc tgatcgtgaa    60
gagatcgtgg gaatggctaa acgtgatggt gtcattgaat accattatcg atcagttgat   120
tctcgttaat ataggcgcca atctgatgt ggcgcttgtg acaagcttca aaaaatggta    180
aggtttacat gaattgtttt gggtacgaat gcgcacacaa actattcgga aaaaaactag   240
aaatctagtt aatacgaagg agcagatcag tc atg gaa aaa cgc gaa ttt aat    293
                                    Met Glu Lys Arg Glu Phe Asn
                                      1               5 att att gca gaa acc ggg atc cac gca cgt ccg gca acc ttg ttg gta    341
Ile Ile Ala Glu Thr Gly Ile His Ala Arg Pro Ala Thr Leu Leu Val
        10                  15                  20 cag gca gca agc aag ttc aac tca gat atc aac ttg gaa tac aag ggt    389
Gln Ala Ala Ser Lys Phe Asn Ser Asp Ile Asn Leu Glu Tyr Lys Gly
 25                  30                  35 aag agc gtt aac ttg aag tct atc atg ggc gtc atg agt ttg ggt gtt    437
Lys Ser Val Asn Leu Lys Ser Ile Met Gly Val Met Ser Leu Gly Val
40                  45                  50                  55 ggc caa ggt gcc gat gtt acc att tct gct gaa ggt gca gac gag gct    485
Gly Gln Gly Ala Asp Val Thr Ile Ser Ala Glu Gly Ala Asp Glu Ala
                60                  65                  70 gat gct atc gct gct att aca gac aca atg aaa aag gaa ggc ttg gct    533
Asp Ala Ile Ala Ala Ile Thr Asp Thr Met Lys Lys Glu Gly Leu Ala
            75                  80                  85 gaa ta atg gct gaa cat ttg aag gga atc gct gct agt gat ggg atc    580
Glu     Met Ala Glu His Leu Lys Gly Ile Ala Ala Ser Asp Gly Ile
             90                  95                 100 gcc aca gcg aag gcc tat tta ctg gtt caa cct gat ttg tca ttc caa    628
Ala Thr Ala Lys Ala Tyr Leu Leu Val Gln Pro Asp Leu Ser Phe Gln
        105                 110                 115 aaa aag acg gtt gat gat cct tca aag gaa atc gat cgc ctg aag cag    676
Lys Lys Thr Val Asp Asp Pro Ser Lys Glu Ile Asp Arg Leu Lys Gln
120                 125                 130 tca ctt gat caa agt aat gat gag tta aag gtt att cga gca aag gcc    724
Ser Leu Asp Gln Ser Asn Asp Glu Leu Lys Val Ile Arg Ala Lys Ala
135                 140                 145                 150 gct gaa tcg ctt ggc gaa gaa gag gct cag gtt ttt gat gcg cac atg    772
Ala Glu Ser Leu Gly Glu Glu Glu Ala Gln Val Phe Asp Ala His Met
                155                 160                 165
```

```
atg att ttg gct gat cct gac ttt act ggt cag gta gag act aag atc    820
Met Ile Leu Ala Asp Pro Asp Phe Thr Gly Gln Val Glu Thr Lys Ile
        170                 175                 180 aag gat gaa aaa gtc aat gct gag cag gct ttg aaa gaa gtc tcc gaa    868
Lys Asp Glu Lys Val Asn Ala Glu Gln Ala Leu Lys Glu Val Ser Glu
185                 190                 195 ttc ttt att aag aca ttc gaa ggt atg acc gac aat cca tat atg cag    916
Phe Phe Ile Lys Thr Phe Glu Gly Met Thr Asp Asn Pro Tyr Met Gln
    200                 205                 210 gaa cgt gcg gct gat gtc cgc gac gtg aca aag cgg atc atg gca cac    964
Glu Arg Ala Ala Asp Val Arg Asp Val Thr Lys Arg Ile Met Ala His
215                 220                 225                 230 ttg ctc ggt cgc aat ttg cca aat cca gca tta att gat gaa gaa gtc   1012
Leu Leu Gly Arg Asn Leu Pro Asn Pro Ala Leu Ile Asp Glu Glu Val
                235                 240                 245 gtt gtg gtt gcg cat gac ctg acc cct tcg gat acc gca caa ttg aat   1060
Val Val Val Ala His Asp Leu Thr Pro Ser Asp Thr Ala Gln Leu Asn
            250                 255                 260 aag aag tat gtc aaa gca ttt gtc acg gat att ggc ggt cgg act gcg   1108
Lys Lys Tyr Val Lys Ala Phe Val Thr Asp Ile Gly Gly Arg Thr Ala
        265                 270                 275 cac agt gcg att atg gca cgt tcg ttg gaa att ccg gct gtt gtt ggg   1156
His Ser Ala Ile Met Ala Arg Ser Leu Glu Ile Pro Ala Val Val Gly
    280                 285                 290 aca gat gac att acc aag aag gct aat aac ggt gat ctt att tcc gtt   1204
Thr Asp Asp Ile Thr Lys Lys Ala Asn Asn Gly Asp Leu Ile Ser Val
295                 300                 305                 310 gat ggc tta act ggt gaa gtt gtt gtt gat ccg acc gat gat gaa gta   1252
Asp Gly Leu Thr Gly Glu Val Val Val Asp Pro Thr Asp Asp Glu Val
                315                 320                 325 gct aag ttc aag cag gat gct gaa gca ttt gct aag caa aaa gct gaa   1300
Ala Lys Phe Lys Gln Asp Ala Glu Ala Phe Ala Lys Gln Lys Ala Glu
            330                 335                 340 tgg gct ctt ttg aag acg gcc aaa tca atc aca gct gat ggc aaa cac   1348
Trp Ala Leu Leu Lys Thr Ala Lys Ser Ile Thr Ala Asp Gly Lys His
        345                 350                 355 ttt gat gtt gct gcc aac atc ggc acg cca aag gat ctt gat ggt gtg   1396
Phe Asp Val Ala Ala Asn Ile Gly Thr Pro Lys Asp Leu Asp Gly Val
    360                 365                 370 ctg gca aac ggt gct gaa ggt atc ggt ttg tat cgg aca gag ttc ttg   1444
Leu Ala Asn Gly Ala Glu Gly Ile Gly Leu Tyr Arg Thr Glu Phe Leu
375                 380                 385                 390 tac atg gat tct gct gaa tta ccg acc gaa gac gat caa ttc gag gcc   1492
Tyr Met Asp Ser Ala Glu Leu Pro Thr Glu Asp Asp Gln Phe Glu Ala
                395                 400                 405 tac aag aag gtt gtc gaa acg atg agt ccg aag cct gtt gtt gtt cgg   1540
Tyr Lys Lys Val Val Glu Thr Met Ser Pro Lys Pro Val Val Val Arg
            410                 415                 420 acg atg gat att ggt ggg gat aaa cat ctg cca tat ttg cca ctt cct   1588
Thr Met Asp Ile Gly Gly Asp Lys His Leu Pro Tyr Leu Pro Leu Pro
        425                 430                 435 gaa gaa cag aac cca ttc ttg ggt tat cgt gcg att cgg atc agt ctt   1636
Glu Glu Gln Asn Pro Phe Leu Gly Tyr Arg Ala Ile Arg Ile Ser Leu
    440                 445                 450 gat cgc caa gat atc ttc cgg aca cag ttg cgc gcc ttg ttg cgt gca   1684
Asp Arg Gln Asp Ile Phe Arg Thr Gln Leu Arg Ala Leu Leu Arg Ala
455                 460                 465                 470 tct gcc ttt ggc aat ctg cgg atc atg ttc cct atg att gct acc att   1732
Ser Ala Phe Gly Asn Leu Arg Ile Met Phe Pro Met Ile Ala Thr Ile
                475                 480                 485
```

```
gct gaa ttc aag caa gca agg cag att ttc act gaa gaa aaa gat aag    1780
Ala Glu Phe Lys Gln Ala Arg Gln Ile Phe Thr Glu Glu Lys Asp Lys
            490                 495                 500 tta gtc aag gat ggc gtc aaa gta tct gat gat atc caa ctt ggc att    1828
Leu Val Lys Asp Gly Val Lys Val Ser Asp Asp Ile Gln Leu Gly Ile
        505                 510                 515 atg atc gaa att cct gca gct gca gtt ttg gct gat cag ttt gct aag    1876
Met Ile Glu Ile Pro Ala Ala Ala Val Leu Ala Asp Gln Phe Ala Lys
    520                 525                 530 tat gtt gac ttc ttc tcc att ggt aca aat gac ttg atc cag tac tct    1924
Tyr Val Asp Phe Phe Ser Ile Gly Thr Asn Asp Leu Ile Gln Tyr Ser
535                 540                 545                 550 atg gcc gct gat cgt ggg aac gag cat gtt tcc tac ctg tat cag cca    1972
Met Ala Ala Asp Arg Gly Asn Glu His Val Ser Tyr Leu Tyr Gln Pro
            555                 560                 565 tac aac cca tcc atc ctt cgc cta atc aag cac gtg att gat tcg gca    2020
Tyr Asn Pro Ser Ile Leu Arg Leu Ile Lys His Val Ile Asp Ser Ala
        570                 575                 580 cat aag gaa ggc aag tgg gcc ggt atg tgt ggc gaa gct gct ggt gat    2068
His Lys Glu Gly Lys Trp Ala Gly Met Cys Gly Glu Ala Ala Gly Asp
    585                 590                 595 cca atc atg gta cca ctg ttg ctt ggt atg ggt ctt gac gaa tac tca    2116
Pro Ile Met Val Pro Leu Leu Leu Gly Met Gly Leu Asp Glu Tyr Ser
600                 605                 610 atg tcc gca act tct gtc ctt aaa gta cgc agc ttg atg aag aag ctt    2164
Met Ser Ala Thr Ser Val Leu Lys Val Arg Ser Leu Met Lys Lys Leu
615                 620                 625                 630 tcg aca gct gat atg gct aag atg gac gaa att gct ttg aac caa aat    2212
Ser Thr Ala Asp Met Ala Lys Met Asp Glu Ile Ala Leu Asn Gln Asn
            635                 640                 645 atc act aat gat gaa aac gct gat ctg gtt aag aaa aca act ggt cag    2260
Ile Thr Asn Asp Glu Asn Ala Asp Leu Val Lys Lys Thr Thr Gly Gln
        650                 655                 660 aaa taaactttca ttatcagaaa gagtctattg actgaataag ttgacggctt         2313
Lys cttttttga ccaaaatttg attttgatcg tgctcgctag cattgatttt tctgaaaccc    2373
gctcgaaaat gggactttat ctttgccatg caaaaaggtg attgcgcgac tatttgtcgg   2433
catctgaaca gtgactgact gcagactttt cagaaaagtg ttaaggttat tatgtaaact   2493
aaaaattgag ttactgattc atggtatggc actgtgagcg gtggttcatt tggacttgta   2553
gggggaattg catgtatcaa tcaaaaacac acaatcatcg atttaccggt caccttgcga   2613
gtgcgaagac acggttgcgg ctagtagcat tgatttcaac gatgggtggc ctgcttttg    2673 gctatgacac tggggtgatc aatggcgcat tgccttttat ttcttcggaa ctgaaacttg   2733
cccctggatc acagggttgg gtcaccagta gcttgacgct gggtgctgct tttggtgcta   2793
tcttagtcgg tcgtttaagt gatcgctatg ggcgcaggcg gctcatcacc atgttagcgg   2853 gcttatttt tctggcaacg gtagcctcgt cactttcccc gagtgctggc tggctgattg    2913
gcgcacggct gatccttgga ttagccgttg gcggcgtctc tgtgctggtt ccaagctttt   2973
tagcagagat tgccccaacg agtcatcgtg ggcggttagt cacacaaaat gagctgatgg   3033
tcgtgactgg ccagttactt gcttttgttc tcaatgcctt tttaggaacc acttttggta   3093
acgttcctgg tatctggcgc tggatgattg tattggcagt cattccggca attatcttag   3153
gtatcgggac ttatttttgtt ccggaatctc ctcgttggtt aatgatgaaa ggacggccgg   3213
cagcagcacg ttcaagtttg gaagtgttgc gatctgctgc tgaagtgcca gcagagattg   3273
```

-continued

| | |
|---|---|
| accatttgaa acagaatctt gccgaagatg ctaaacataa gcaggcgagt gttcgagcat | 3333 |
| tgaaaaccaa atggattcgc cgactggttc tgattggcat cggcctaggc gtcattcagc | 3393 |
| aaattgctgg tatcaatgtc atgatgtatt atggcacctc aatttttacaa atgacgggtt | 3453 |
| ttgggcgaga tagcgccttg atcgccaaca ttgccaatgg ggttactgcc gttgctgcaa | 3513 |
| cgattgtgac gttgcaattg ttgaagcatg ttccgcggcg gccaatgctg attgtgggat | 3573 |
| tgattggctc aaccgtggcg attactggtg tcaccttcgc tagtcgacta ccagcgggtt | 3633 |
| cgccattccg ggcatttgcg acaatcggga tgatgatgct gttcttggcg ttcttccaag | 3693 |
| gcgctatcag tccaatgact tggctgctga tgtctgaaat cttccctgaa caggttcggg | 3753 |
| gcatagggat gggcgctgca accttctgct tgtggttagc taactttggt gttggcgttc | 3813 |
| tgttcccgat tggtctggcc caaataggca tgttctggac attcgtttgc ttcatcggga | 3873 |
| caaatttgat tcattgctt ttcgttctga tttttgtgcc ggaaacggct ggacgctccc | 3933 |
| tcgaaacttt gcaccgagag gagaaagccc gcttaaatca ttaatgacaa gcgatttgtt | 3993 |
| caagaccaaa aagttgcgct ttacaaaaag tttgatacca taaggtgta tcaacaattc | 4053 |
| gatgaacctt cacaaagggg agccattggc tgagaacggg gaaacccgga cccttcgaac | 4113 |
| ctgttcgtta atgcgagcgt agggatttgt gaatggt | 4150 |

<210> SEQ ID NO 2
<211> LENGTH: 88
<212> TYPE: PRT
<213> ORGANISM: Lactobacillus casei

<400> SEQUENCE: 2

Met Glu Lys Arg Glu Phe Asn Ile Ile Ala Glu Thr Gly Ile His Ala
1               5                   10                  15

Arg Pro Ala Thr Leu Leu Val Gln Ala Ala Ser Lys Phe Asn Ser Asp
                20                  25                  30

Ile Asn Leu Glu Tyr Lys Gly Lys Ser Val Asn Leu Lys Ser Ile Met
            35                  40                  45

Gly Val Met Ser Leu Gly Val Gly Gln Gly Ala Asp Val Thr Ile Ser
        50                  55                  60

Ala Glu Gly Ala Asp Glu Ala Asp Ala Ile Ala Ala Ile Thr Asp Thr
65                  70                  75                  80

Met Lys Lys Glu Gly Leu Ala Glu
                85

<210> SEQ ID NO 3
<211> LENGTH: 575
<212> TYPE: PRT
<213> ORGANISM: Lactobacillus casei

<400> SEQUENCE: 3

Met Ala Glu His Leu Lys Gly Ile Ala Ala Ser Asp Gly Ile Ala Thr
1               5                   10                  15

Ala Lys Ala Tyr Leu Leu Val Gln Pro Asp Leu Ser Phe Gln Lys Lys
                20                  25                  30

Thr Val Asp Asp Pro Ser Lys Glu Ile Asp Arg Leu Lys Gln Ser Leu
            35                  40                  45

Asp Gln Ser Asn Asp Glu Leu Lys Val Ile Arg Ala Lys Ala Ala Glu
        50                  55                  60

Ser Leu Gly Glu Glu Glu Ala Gln Val Phe Asp Ala His Met Met Ile
65                  70                  75                  80

Leu Ala Asp Pro Asp Phe Thr Gly Gln Val Glu Thr Lys Ile Lys Asp

-continued

```
                85                  90                  95
Glu Lys Val Asn Ala Glu Gln Ala Leu Lys Glu Val Ser Glu Phe Phe
            100                 105                 110

Ile Lys Thr Phe Glu Gly Met Thr Asp Asn Pro Tyr Met Gln Glu Arg
            115                 120                 125

Ala Ala Asp Val Arg Asp Val Thr Lys Arg Ile Met Ala His Leu Leu
            130                 135                 140

Gly Arg Asn Leu Pro Asn Pro Ala Leu Ile Asp Glu Val Val Val
145                 150                 155                 160

Val Ala His Asp Leu Thr Pro Ser Asp Thr Ala Gln Leu Asn Lys Lys
                165                 170                 175

Tyr Val Lys Ala Phe Val Thr Asp Ile Gly Arg Thr Ala His Ser
                180                 185                 190

Ala Ile Met Ala Arg Ser Leu Glu Ile Pro Ala Val Val Gly Thr Asp
            195                 200                 205

Asp Ile Thr Lys Lys Ala Asn Asn Gly Asp Leu Ile Ser Val Asp Gly
            210                 215                 220

Leu Thr Gly Glu Val Val Asp Pro Thr Asp Glu Val Ala Lys
225                 230                 235                 240

Phe Lys Gln Asp Ala Glu Ala Phe Ala Lys Gln Lys Ala Glu Trp Ala
                245                 250                 255

Leu Leu Lys Thr Ala Lys Ser Ile Thr Ala Asp Gly Lys His Phe Asp
                260                 265                 270

Val Ala Ala Asn Ile Gly Thr Pro Lys Asp Leu Asp Gly Val Leu Ala
                275                 280                 285

Asn Gly Ala Glu Gly Ile Gly Leu Tyr Arg Thr Glu Phe Leu Tyr Met
290                 295                 300

Asp Ser Ala Glu Leu Pro Thr Glu Asp Asp Gln Phe Glu Ala Tyr Lys
305                 310                 315                 320

Lys Val Val Glu Thr Met Ser Pro Lys Pro Val Val Arg Thr Met
                325                 330                 335

Asp Ile Gly Gly Asp Lys His Leu Pro Tyr Leu Pro Leu Pro Glu Glu
            340                 345                 350

Gln Asn Pro Phe Leu Gly Tyr Arg Ala Ile Arg Ile Ser Leu Asp Arg
            355                 360                 365

Gln Asp Ile Phe Arg Thr Gln Leu Arg Ala Leu Leu Arg Ala Ser Ala
            370                 375                 380

Phe Gly Asn Leu Arg Ile Met Phe Pro Met Ile Ala Thr Ile Ala Glu
385                 390                 395                 400

Phe Lys Gln Ala Arg Gln Ile Phe Thr Glu Glu Lys Asp Lys Leu Val
                405                 410                 415

Lys Asp Gly Val Lys Val Ser Asp Asp Ile Gln Leu Gly Ile Met Ile
                420                 425                 430

Glu Ile Pro Ala Ala Ala Val Leu Ala Asp Gln Phe Ala Lys Tyr Val
                435                 440                 445

Asp Phe Phe Ser Ile Gly Thr Asn Asp Leu Ile Gln Tyr Ser Met Ala
450                 455                 460

Ala Asp Arg Gly Asn Glu His Val Ser Tyr Leu Tyr Gln Pro Tyr Asn
465                 470                 475                 480

Pro Ser Ile Leu Arg Leu Ile Lys His Val Ile Asp Ser Ala His Lys
                485                 490                 495

Glu Gly Lys Trp Ala Gly Met Cys Gly Glu Ala Ala Gly Asp Pro Ile
                500                 505                 510
```

```
Met Val Pro Leu Leu Leu Gly Met Gly Leu Asp Glu Tyr Ser Met Ser
            515                 520                 525

Ala Thr Ser Val Leu Lys Val Arg Ser Leu Met Lys Lys Leu Ser Thr
        530                 535                 540

Ala Asp Met Ala Lys Met Asp Glu Ile Ala Leu Asn Gln Asn Ile Thr
545                 550                 555                 560

Asn Asp Glu Asn Ala Asp Leu Val Lys Lys Thr Thr Gly Gln Lys
                565                 570                 575

<210> SEQ ID NO 4
<211> LENGTH: 21
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (9)..(9)
<223> OTHER INFORMATION: n = a or g
<220> FEATURE:
<221> NAME/KEY: misc_feature
<222> LOCATION: (12)..(12)
<223> OTHER INFORMATION: n = any nucleotide
<220> FEATURE:
<221> NAME/KEY: misc_feature
<222> LOCATION: (15)..(15)
<223> OTHER INFORMATION: n = a or g
<220> FEATURE:
<221> NAME/KEY: misc_feature
<222> LOCATION: (18)..(18)
<223> OTHER INFORMATION: n = c or t
<220> FEATURE:
<221> NAME/KEY: misc_feature
<222> LOCATION: (21)..(21)
<223> OTHER INFORMATION: n = c or t

<400> SEQUENCE: 4
atggaaaanc nganttnaa n                                            21

<210> SEQ ID NO 5
<211> LENGTH: 26
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (6)..(6)
<223> OTHER INFORMATION: n = any nucleotide
<220> FEATURE:
<221> NAME/KEY: misc_feature
<222> LOCATION: (9)..(9)
<223> OTHER INFORMATION: n = a or g
<220> FEATURE:
<221> NAME/KEY: misc_feature
<222> LOCATION: (12)..(12)
<223> OTHER INFORMATION: n = c or t
<220> FEATURE:
<221> NAME/KEY: misc_feature
<222> LOCATION: (15)..(15)
<223> OTHER INFORMATION: n = a or t
<220> FEATURE:
<221> NAME/KEY: misc_feature
<222> LOCATION: (18)..(18)
<223> OTHER INFORMATION: n = c or t
<220> FEATURE:
<221> NAME/KEY: misc_feature
<222> LOCATION: (20)..(20)
<223> OTHER INFORMATION: n = a or g
<220> FEATURE:
<221> NAME/KEY: misc_feature
<222> LOCATION: (21)..(21)
<223> OTHER INFORMATION: n = a or g
<220> FEATURE:
```

```
<221> NAME/KEY: misc_feature
<222> LOCATION: (24)..(24)
<223> OTHER INFORMATION: n = a or g

<400> SEQUENCE: 5
gccatngtnt antgnatnan ntcntt                                          26

<210> SEQ ID NO 6
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = a or g
<220> FEATURE:
<221> NAME/KEY: misc_feature
<222> LOCATION: (6)..(6)
<223> OTHER INFORMATION: n = any nucleotide
<220> FEATURE:
<221> NAME/KEY: misc_feature
<222> LOCATION: (7)..(7)
<223> OTHER INFORMATION: n = c or g
<220> FEATURE:
<221> NAME/KEY: misc_feature
<222> LOCATION: (9)..(9)
<223> OTHER INFORMATION: n = any nucleotide
<220> FEATURE:
<221> NAME/KEY: misc_feature
<222> LOCATION: (12)..(12)
<223> OTHER INFORMATION: n = any nucleotide
<220> FEATURE:
<221> NAME/KEY: misc_feature
<222> LOCATION: (15)..(15)
<223> OTHER INFORMATION: n = a or g
<220> FEATURE:
<221> NAME/KEY: misc_feature
<222> LOCATION: (18)..(18)
<223> OTHER INFORMATION: n = any nucleotide

<400> SEQUENCE: 6
ccntcnnang cngcnatncc                                                 20

<210> SEQ ID NO 7
<211> LENGTH: 31
<212> TYPE: DNA
<213> ORGANISM: Artificial Sequence
<220> FEATURE:
<223> OTHER INFORMATION: Synthetic DNA

<400> SEQUENCE: 7
aagagcgtta acttgaaggc tatcatgggc g                                    31

<210> SEQ ID NO 8
<211> LENGTH: 31
<212> TYPE: DNA
<213> ORGANISM: Artificial Sequence
<220> FEATURE:
<223> OTHER INFORMATION: Synthetic DNA

<400> SEQUENCE: 8
aagagcgtta acttgaagac tatcatgggc g                                    31

<210> SEQ ID NO 9
<211> LENGTH: 31
<212> TYPE: DNA
<213> ORGANISM: Artificial Sequence
<220> FEATURE:
<223> OTHER INFORMATION: Synthetic DNA
```

```
<400> SEQUENCE: 9
aagagcgtta acttgaagga tatcatgggc g                               31

<210> SEQ ID NO 10
<211> LENGTH: 31
<212> TYPE: DNA
<213> ORGANISM: Artificial Sequence
<220> FEATURE:
<223> OTHER INFORMATION: Synthetic DNA

<400> SEQUENCE: 10
aagagcgtta acttgaagtc taccatgggc g                               31

<210> SEQ ID NO 11
<211> LENGTH: 20
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (3)..(3)
<223> OTHER INFORMATION: n = any nucleotide
<220> FEATURE:
<221> NAME/KEY: misc_feature
<222> LOCATION: (4)..(4)
<223> OTHER INFORMATION: n = a or g
<220> FEATURE:
<221> NAME/KEY: misc_feature
<222> LOCATION: (6)..(6)
<223> OTHER INFORMATION: n = any nucleotide
<220> FEATURE:
<221> NAME/KEY: misc_feature
<222> LOCATION: (9)..(9)
<223> OTHER INFORMATION: n = any nucleotide
<220> FEATURE:
<221> NAME/KEY: misc_feature
<222> LOCATION: (12)..(12)
<223> OTHER INFORMATION: n = a or g
<220> FEATURE:
<221> NAME/KEY: misc_feature
<222> LOCATION: (15)..(15)
<223> OTHER INFORMATION: n = c or t
<220> FEATURE:
<221> NAME/KEY: misc_feature
<222> LOCATION: (18)..(18)
<223> OTHER INFORMATION: n = a or g

<400> SEQUENCE: 11
ggnntnggna anagnganac                                            20

<210> SEQ ID NO 12
<211> LENGTH: 18
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(1)
<223> OTHER INFORMATION: n = a or g
<220> FEATURE:
<221> NAME/KEY: misc_feature
<222> LOCATION: (4)..(4)
<223> OTHER INFORMATION: n = a or g
<220> FEATURE:
<221> NAME/KEY: misc_feature
<222> LOCATION: (7)..(7)
<223> OTHER INFORMATION: n = any amino acid
<220> FEATURE:
<221> NAME/KEY: misc_feature
<222> LOCATION: (13)..(13)
<223> OTHER INFORMATION: n = any amino acid
<220> FEATURE:
```

<221> NAME/KEY: misc_feature
<222> LOCATION: (16)..(16)
<223> OTHER INFORMATION: n = any amino acid
<220> FEATURE:
<221> NAME/KEY: misc_feature
<222> LOCATION: (16)..(16)
<223> OTHER INFORMATION: n = any nucleotide

<400> SEQUENCE: 12
naanttnccc cancgncc                                                    18

<210> SEQ ID NO 13
<211> LENGTH: 35
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (18)..(18)
<223> OTHER INFORMATION: n = any amino acid
<220> FEATURE:
<221> NAME/KEY: misc_feature
<222> LOCATION: (21)..(21)
<223> OTHER INFORMATION: n = any amino acid
<220> FEATURE:
<221> NAME/KEY: misc_feature
<222> LOCATION: (21)..(21)
<223> OTHER INFORMATION: n = any nucleotide
<220> FEATURE:
<221> NAME/KEY: misc_feature
<222> LOCATION: (24)..(24)
<223> OTHER INFORMATION: n = c or t
<220> FEATURE:
<221> NAME/KEY: misc_feature
<222> LOCATION: (27)..(27)
<223> OTHER INFORMATION: n = c or t
<220> FEATURE:
<221> NAME/KEY: misc_feature
<222> LOCATION: (28)..(28)
<223> OTHER INFORMATION: n = a or g
<220> FEATURE:
<221> NAME/KEY: misc_feature
<222> LOCATION: (30)..(30)
<223> OTHER INFORMATION: n = c or t
<220> FEATURE:
<221> NAME/KEY: misc_feature
<222> LOCATION: (33)..(33)
<223> OTHER INFORMATION: n = c or t

<400> SEQUENCE: 13
ataaagcttg anmtgacngg ntanttnnan twnta                                 35

<210> SEQ ID NO 14
<211> LENGTH: 26
<212> TYPE: DNA
<213> ORGANISM: Artificial Sequence
<220> FEATURE:
<223> OTHER INFORMATION: Synthetic DNA

<400> SEQUENCE: 14
attgaaaaga gctcggatta agtgct                                           26

<210> SEQ ID NO 15
<211> LENGTH: 32
<212> TYPE: DNA
<213> ORGANISM: Artificial Sequence
<220> FEATURE:
<223> OTHER INFORMATION: Synthetic DNA -continued

```
<400> SEQUENCE: 15
cccctcgagg tcgacggtat ggataagctt ga                                    32

<210> SEQ ID NO 16
<211> LENGTH: 33
<212> TYPE: DNA
<213> ORGANISM: Artificial Sequence
<220> FEATURE:
<223> OTHER INFORMATION: Synthetic DNA

<400> SEQUENCE: 16
catgacatcg ataatgccct agccacgaat ttc                                   33

<210> SEQ ID NO 17
<211> LENGTH: 22
<212> TYPE: DNA
<213> ORGANISM: Artificial Sequence
<220> FEATURE:
<223> OTHER INFORMATION: Synthetic DNA

<400> SEQUENCE: 17
gtgggatcca tggcagacag cg                                               22

<210> SEQ ID NO 18
<211> LENGTH: 21
<212> TYPE: DNA
<213> ORGANISM: Artificial Sequence
<220> FEATURE:
<223> OTHER INFORMATION: Synthetic DNA

<400> SEQUENCE: 18
tacggtacca atgaacttcc a                                                21

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Met Glu Lys Arg Glu Phe Asn
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 20

Asn Asp Leu Ile Gln Tyr Thr Met Ala
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 21

Gly Ile Ala Ala Ser Asp Gly
1               5
```

MUTANTS OF *LACTOBACILLUS CASEI* DEFECTIVE IN CARBON CATABOLISM REGULATION

CONTINUATION DATA

This application is a Divisional of U.S. application Ser. No. 10/240,280, filed on Jan. 27, 2003 now abandoned, which is the National Stage of PCT/EP01/03951, filed on Mar. 30, 2001.

The present invention relates to mutant strains of bacteria of the group *Lactobacillus casei* defective in a carbon catabolism regulation pathway, and to their use in the processing of fermented foods.

As defined herein, the group *Lactobacillus casei* includes the species *L. casei*, as well as the species *L. paracasei* (formerly *L. casei* subsp. *paracasei*), *L. rhamnosus* (formerly *L. casei* subsp. *rhamnosus*) and *L. zeae*. Those species are phylogenetically very closely related to each other and their respective 16S and 23S rDNA genes always show a similarity greater than 97.5% [MORI et al., Int. J. Syst. Bacteriol., 47, 54-57, (1997)].

*L. casei* is recognized as a probiotic, i.e. a live microbial feed supplement having a positive effect on the health of the consumer, and is widely used as a starter in dairy industry and in the preparation of fermented food, more specifically food containing living ferments.

Carbon catabolite repression (CCR) is a regulatory mechanism allowing bacteria to choose between different carbon sources according to their metabolic value and to switch from a carbon source to another depending on their availability in the growth medium. A well-known manifestation of catabolic repression is the diauxic growth that occurs when bacteria are grown in presence of both glucose and lactose. Diauxic growth curves show two distinct phases of exponential growth, separated by a lag phase. During the first phase of growth, glucose represses the synthesis of the enzymes necessary for lactose utilisation, and is therefore the only source of energy of the bacteria. When all the glucose is exhausted occurs the lag phase, during which the enzymes for lactose utilisation are synthesised, allowing lactose to be used as a source of energy during the second phase of growth.

A main target of catabolite repression is the transport of sugars into the bacterial cell. In *L. casei*, this transport is predominantly performed by the phosphoenolpyruvate:carbohydrate phosphotransferase system (PTS).

The PTS of gram-positive bacteria has been studied mainly in *Bacillus subtilis*; it has been shown that it effects the phosphorylation of sugars and their transfer into the cell through a cascade of phosphorylations involving the general non-sugar-specific enzymes EI and HPr, and the sugar-specific enzymes EIIA, EIIB, and EIIC. The first step is the phosphorylation of EI from phosphoenolpyruvate (PEP). The phosphorylated EI (EI-P) catalyses the phosphorylation of HPr, at the catalytic His-15. HPr phosphorylated at His-15 (designated as P-His-HPr) transfers its phosphoryl group to EIIA, which in turn phosphorylates EIIB. Phosphorylated EIIB (P-EIIB) associated with the membrane protein EIIC, catalyses the simultaneous uptake and phosphorylation of a specific carbohydrate.

It has been shown that components of the PTS, and more specifically the enzyme HPr, are also involved in other regulatory pathways.

For instance, P-His-HPr can transfer its phosphoryl group also to non-PTS proteins, such as glycerol kinase [CHARRIER et al., J. Biol. Chem., 272, 14166-14174, (1997)] or antiterminators and transcriptional activators possessing the PTS regulation domain (PRD) which contains several phosphorylation sites recognised by P-His-HPr [TORTOSA et al., J. Biol. Chem., 272, 17230-17237, (1997); STÜLKE et al., Mol. Microbiol., 28, 865-874, (1998); LINDNER et al., Mol. Microbiol., 31, 995-1006, (1999)]. In all cases, P-His-HPr-dependent phosphorylation leads to the activation of the function of the non-PTS proteins and this phosphorylation has been shown to serve as a secondary carbon catabolite repression mechanism in Gram-positive bacteria [DEUTSCHER at al., J. Bacteriol., 175, 3730-3733, (1993); KRÜGER et al., J. Bacteriol., 178, 2637-2644, (1996); MARTIN-VERSTRAETE et al., Mol. Microbiol., 28, 293-303, (1998)]. In *Lactobacillus casei*, the antiterminator LacT, which regulates the expression of the lac operon, contains two PRD and seems to be controlled by this mechanism.

In Gram-positive bacteria, HPr may also be phosphorylated by the bifunctional HPr kinase/phosphatase HprK [GALINIER at al., Proc. Natl. Acad. Sci. USA, 95, 1823-1828, (1998); REIZER et al., Mol. Microbiol., 27, 1157-1169, (1998); BROCHU and VADEBONCOEUR, J. Bacteriol., 181, 709-717, (1999); KRAVANJA et al., Mol. Microbiol., 31, 59-66, (1999)]. In *Bacillus subtilis*, this phosphorylation, which occurs at the regulatory Ser-46 [DEUTSCHER et al., Biochemistry, 25, 6543-6551, (1986)], is stimulated by fructose-1,6-bisphosphate and inhibited by inorganic phosphate [GALINIER et al., Proc. Natl. Acad. Sci. USA, 95, 1823-1828, (1998)]. HPr phosphorylated at Ser-46 (designated as P-Ser-HPr), participates in the major mechanism of CCR/carbon catabolite activation operative in bacilli and presumably other Gram-positive bacteria [DEUTSCHER et al., Mol. Microbiol., 42, 171-178, (1997)]. It functions as corepressor for the catabolite control protein CcpA, a member of the LacI/GalR family of transcriptional repressors/activators [HENKIN et al., Mol. Microbiol., 5, 575-584, (1991)]. The complex formed between CcpA and P-Ser-HPr has been shown to bind to catabolite response elements (cre) [FUJITA and MIWA, J. Bacteriol., 176, 511-513, (1994); GÖSSERINGER et al., J. Mol. Biol., 266, 665-676, (1997); KIM at al., Proc. Natl. Acad. Sci. USA, 95, 9590-9595, (1998); GALINIER at al., J. Mol. Biol., 286, 307-314, (1999); MARTIN-VERSTRAETE et al., Mol. Microbiol., 28, 293-303, (1999)], operator sites preceding or overlapping the promoters or being located within the 5' region of catabolite repressed genes and operons [HUECK et al., Res. Microbiol., 145, 503-518, (1994)]. For instance, a functional cre element is found in the promoter region of the lactose operon lacTEGF of *L. casei*, which comprises the genes lacE and lacF encoding respectively the lactose transport enzymes EIICB$^{Lac}$ and EIIA$^{Lac}$ together with genes encoding an antiterminator protein (lacT), and a phospho-beta-galactosidase (lacG) [GOSALBES et al., J. Bacteriol., 181, 3928-3934, (1999)].

Genes encoding components of CCR system, and more specifically genes related to the PTS, such as ptsI and ptsH encoding respectively the enzymes EI and HPr of the PTS system, hprK encoding the HPr kinase/phosphatase, and ccpA have been characterised in some species of Gram-positive bacteria.

In *L. casei*, the gene ccpA [MONEDERO et al., J. Bacteriol., 179, 6657-6664, (1997)], and the genes lacT, lacE, lacG and lacF [GOSALBES et al., referred above; POTER and CHASSY, Gene, 62, 263-276, (1988); ALPERT and CHASSY, Gene, 62, 277-288, (1988); ALPERT and CHASSY, J. Biol. Chem., 265, 22561-22568, (1990); ALPERT and SIEBERS, J. Bacteriol., 179, 1555-1562, (1997)], have been cloned and characterised until now.

The inventors have recently identified, cloned and sequenced the ptsI, ptsH and hprK genes of *L. casei*.

The nucleotidic sequence of the ptsHI operon, and the peptidic sequences of HPr and EI of *L. casei* are respectively disclosed in the enclosed sequence listing under the identifiers SEQ ID NO: 1, SEQ ID NO: 2, and SEQ ID NO: 3. The sequence of the hprK gene is available in GENBANK under the access number Y18948.

The inventors have now studied the effect of mutations in ptsI, ptsH and hprK, as well as the effect of mutations in ccpA on growth and metabolic properties of *L. casei*. They found that, surprisingly, *L. casei* strains having mutations impairing the regulation of carbon catabolite repression mechanisms involving the PTS enzyme HPr, and more specifically mutations impairing the regulation of the PTS, and/or mutations impairing the transcriptional regulation of catabolite repressed genes through the binding of the complex CcpA/P-Ser-HPr, possess an improved capacity to produce compounds useful in the food industry, such as aroma compounds and/or polysaccharides.

An object of the present invention is the use of a mutant of *L. casei* having at least a mutation impairing the regulation of a carbon catabolite repression mechanism involving the PTS enzyme HPr, for the preparation of a food product.

BRIEF DESCRIPTION OF THE DRAWINGS

In FIG. 2A, integrants obtained by the first (1) and second (2) type of recombination exhibited a lac⁻ phenotype, whereas integrants obtained by the third type of recombination (3) could slowly ferment lactose (probably due to a readthrough from a plasmid-located promoter). The three different DNA arrangements presented under: "2$^{nd}$ recombination" (shown on FIG. 2C) are obtained from type 3 integrants after a second recombination event leading to the excision of the pVMH plasmid. 3a provides a lac⁻ strain having a frame shift mutation in ptsI; 3b provides a wild-type strain (lac⁺); 3c provides the desired ptsH mutant (lac⁺).

Figure 1:
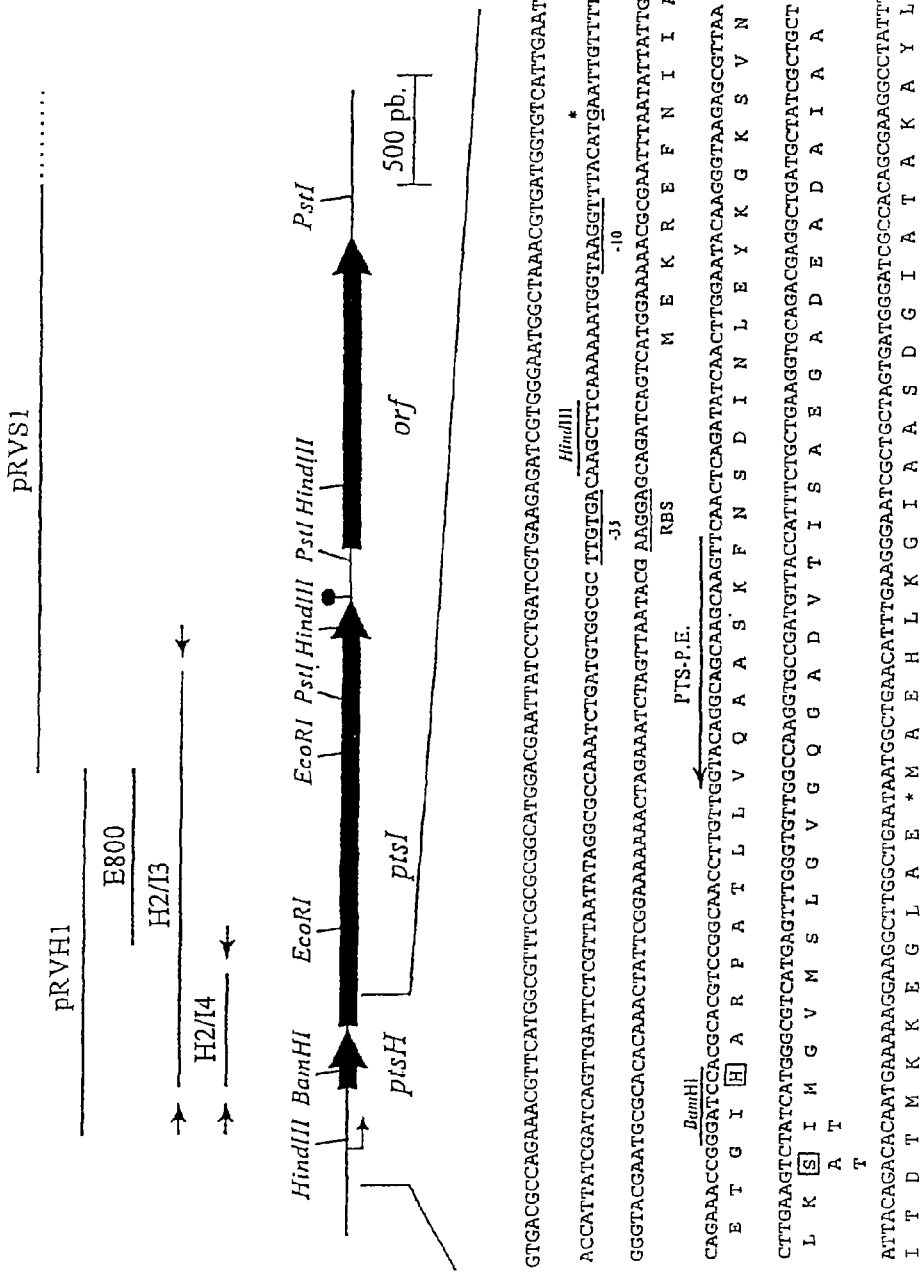
FIG. 1: a schematic representation of the sequenced chromosomal *L. casei* DNA fragment containing the ptsHI operon. Indicated are the three ORF's detected in this fragment, the promoter and terminator of the ptsHI operon and several important restriction sites. The initially isolated PCR fragments H2/I4 and H2/I3 (flanked by inverted arrows) and the 865 bp EcoRI fragment, which was called E800 and subcloned into pRV300, are shown above the schematic presentation of the total DNA fragment, nucleotides shown in SEQ ID NO: 1, amino acids, residues 1-109 in SEQ ID NO: 1.

Preferably, said mutant is selected from the group consisting of:

a) mutants having at least a mutation impairing the regulation of CCR through P-His-HPr;

b) mutants having at least a mutation impairing the regulation of CCR through P-Ser-HPr.

Mutations of sub-group a) include in particular:

mutations in genes encoding the components of the PTS, for instance: any mutation in the ptsH gene impairing the ability of HPr to be phosphorylated at His-15, or to phosphorylate EIIA; any mutation in the ptsI gene impairing the ability of EI to phosphorylate HPr at His-15; any mutation in a gene encoding an enzyme EIIA, EIIB, or EIIC impairing the transfer of a phosphoryl group to a carbohydrate;

mutations in genes encoding antiterminators or transcriptional activators having the PTS regulation domain, for instance any mutation impairing the phosphorylation of any of these antiterminators or transcriptional activators by P-His-HPr and/or by P-EIIB or mimicking the phosphorylated form of the antiterminator (for example phosphorylatable histidyl residues mutated to Asp or Glu);

mutations destroying terminators located in front of genes regulated by antiterminators which are phosphorylated and controlled by P-His-HPr and/or by P-EIIB.

Mutations of sub-group b) include in particular: any mutation in the ptsH gene impairing the ability of HPr to be phosphorylated at Ser-46; any mutation in the hprK gene impairing the ability of HprK to phosphorylate HPr at Ser-46; any mutation in the ptsH gene or in the ccpA gene impairing the formation of a complex between CcpA and P-Ser-HPr or the binding of said complex to cre elements; any mutation in said cre elements impairing their ability to bind said CcpA/P-Ser-HPr complex.

Non-limitative examples of mutants of *L. casei* which can be used according to the invention are:

mutants having at least a mutation in the ptsI gene resulting in the lack of expression of enzyme EI, or in the expression of an enzyme EI devoid of at least an active domain of wild-type EI. For instance, a mutant of the invention may be obtained by introduction of a frameshift mutation at location 870 of the sequence SEQ ID NO: 1. The insertion of four nucleotides (sequence AATT) at this location results in a stop codon four codons after the site of insertion. This results in the expression of a truncated EI protein devoid of at least aminoacids 110 to 574 of wild-type EI, with the addition of four new codons before the first translational stop codon.

mutants having at least a mutation in the hprK gene resulting in the lack of expression of HprK or in the expression of a HprK devoid of at least an active domain of wild-type HprK. For instance, a mutant of the invention may be devoid of at least aminoacids 208 to 319 of wild-type HprK.

mutants having at least a mutation in the ccpA gene resulting in the lack of expression of CcpA or in the expression of a CcpA devoid of at least an active domain of wild-type CcpA. For instance, a mutant of the invention may be obtained by introduction of a frameshift mutation at location 710 of the sequence U28137 of GENBANK. The insertion of four nucleotides (sequence AATT) at this location results in a stop codon five codons after the site of insertion, and in the expression of a CcpA devoid of at least aminoacids 134 to 333 of wild-type CcpA.

mutants in the ptsH gene having at least a mutation resulting in the lack of expression of HPr or in the expression of a HPr having at least one amino-acid substitution at position 15 and/or at position 46 and/or at position 47 of wild-type HPr, and/or at least a mutation resulting in the expression of a HPr deleted of at least one of aminoacids 15, 46, and/or 47 of wild-type HPr.

The invention also provides:

mutants of *L. casei* having at least one mutation in at least one of ptsI, or ptsH genes, wherein said mutation impairs at least one of the functions of the product of said gene;

food-grade mutants of *L. casei*, having at least one mutation impairing at least one of the functions of a gene involved in the regulation of a carbon catabolite repression mechanism through the PTS enzyme HPr. This includes more particularly food-grade mutants having at least one mutation in any of ptsI, ptsH, hprK, or ccpA genes.

"Food-grade mutants" are herein defined as mutant bacteria acceptable for use in preparation of food. To be food-grade, the mutants must not comprise sequences derived from microorganisms other than the ones used in food industry. Preferably, they must not comprise sequences derived from microorganisms other than those belonging to the species from which the mutant derives. Also they must not comprise potentially harmful DNA sequences such as antibiotic resistance genes.

*L. casei* mutants of ccpA gene [MONEDERO et al., J. Bacteriol., 179, 6657-6664, (1997)] were already known in the art; however they were not food-grade mutants.

Mutants of the invention may be obtained by the conventional molecular biology methods. From the sequences of *L. casei* genes such as ptsI, ptsH, hprK or other *L. casei* genes known in the art, such as ccpA, the skilled artisan can easily design tools allowing to perform the desired mutations through directed mutagenesis. Said mutations may be obtained by the insertion, deletion, and/or substitution of one nucleotide or of several nucleotides, adjacent or not.

Said mutations may for instance be obtained by the deletion of said regulatory DNA sequence or of the said insertion, deletion, and/or substitution of one nucleotide or of several nucleotides, adjacent or not.

Such mutations include in particular any mutation resulting in the production of a protein having at least one deletion, insertion, or non-conservative substitutions of one or several amino acid residues in a domain essential for the biological activity of said protein.

The mutant gene thus obtained is then cloned into a vector, preferably an expression vector, and used to transform *L. casei* host cells by any appropriate method, known in itself. Methods and vectors suitable for the transformation of *L. casei* are for instance disclosed by POSNO et al. [Appl. Environ. Microbiol., 57, 1822-1828, (1991)].

By way of example, one can use an extrachromosomal vector able to replicate in *L. casei*. However, in order to obtain stable mutants, a vector allowing the integration of the mutant gene into the chromosome of *L. casei* will be preferred.

Integration of the mutant gene into the bacterial chromosome occurs by recombination of the vector genetic material at a homologous site (generally the wild-type allele of the mutant gene) on the bacterial chromosome. Integration may result from a single or double recombination event. Single recombination events result in integration of the entire vector. Double recombination events lead to the excision of the exogenous vector sequences.

By way of example, a method for integration of a mutant lacT, lacE, or lacF gene in the chromosome of *L. casei* is disclosed by GOSALBES et al. [J. Bacteriol. 181, 3928-3934, (1999)]. This method includes cloning a wild-type gene in an integrative plasmid (pRV300, having an $Erm^R$ marker), inducing a mutation in the cloned gene (for example by cutting the gene with a restriction enzyme and by introducing a mutation by making the restriction site blunt-end), transforming *L. casei* with the plasmid comprising the mutated gene, culturing the bacteria in selective medium containing erythromycin in order to select the bacteria having integrated the plasmid by a single recombination event (which are $Erm^R$). Further cultivation of these $Erm^R$ bacteria in non-selective medium (i.e. without erythromycin) allows to obtain bacteria having undergone a double recombination event leading to the excision of the vector sequences.

Such a method can be used, for instance, for obtaining food-grade mutants wherein the function of EI, HPr, HprK, or CcpA is completely or partially impaired. This method comprises:

transforming *L. casei* with an integrative vector comprising a mutated gene selected among ptsI, ptsH, hprK, or ccpA, and further comprising a selective marker gene;

culturing the bacteria under selective conditions for the marker gene (for instance, if the marker gene is an antibiotic resistance gene, in presence of the corresponding antibiotic) and recovering the bacteria able to grow in these conditions, i.e. having integrated the vector into their chromosome by a single recombination event;

culturing said bacteria under non-selective conditions for the marker gene in order to obtain bacteria having undergone a double recombination event leading to the excision of the vector sequences.

This double recombination event produces bacteria having a wild-type phenotype and bacteria having the desired mutation. The latter can then be screened on the basis of their phenotypic properties, and/or by PCR amplification of the chromosomic region wherein the mutation was targeted and analysis of the amplification products (for instance comparison of the restriction profiles). The presence of the desired mutation can further be confirmed by DNA sequencing.

A preferred method for obtaining food-grade mutants wherein the catalytic function of HPr is only slightly impaired comprises:
transforming a mutant strain of L. casei wherein the ptsI gene is inactivated in such a way that function of EI is totally impaired, with an integrative vector comprising a ptsHI operon consisting of a wild type ptsI gene and the mutant ptsH gene, and further comprising a selective marker gene;
culturing the transformed bacteria on lactose under selective conditions for the marker gene, and recovering the bacteria having integrated the vector into their chromosome by a single recombination event;
culturing the selected bacteria on lactose and under non-selective conditions for the marker gene in order to obtain bacteria having undergone a double recombination event leading to the excision of the vector sequences.

Clones containing an intact ptsI gene and a mutated ptsH gene can be selected on the basis of their slightly reduced growth on lactose. The presence of the mutation can be confirmed by DNA sequencing.

Mutant strains of the invention can also be obtained from wild-type strains of L. casei through classical mutation methods, for instance chemical or UV induced mutagenesis. They can also be naturally occurring mutants isolated from L. casei populations.

For instances, reporter gene fusions to catabolite repressed or activated genes could be used to identify ccpA, ptsH or hprK mutants defective in carbon catabolite repression or carbon catabolite activation.

Mutant strains of the invention may also be selected on the basis of their metabolic properties. For instance: mutants in the ptsI or ptsH gene may be selected on the basis of their resistance to 2-deoxy glucose. Mutants in the ptsI gene or mutants in the ptsH gene having an inactive EI or HPr, respectively, may also be selected on the basis of their ability to grow on non-PTS sugar but not on PTS sugars.

The invention also provides a process for preparing a food product or food additive wherein said process comprises fermenting a food substrate with a mutant strain of L. casei, as defined above.

Preferably said food product is a dairy product.

According to a preferred embodiment, the process of the invention comprises preparing a food product enriched with aroma compounds (such as acetate, acetoin, diacetyl, hydroxy-3-pentanone, propionate) by fermenting a food substrate with a strain of L. casei having a mutation impairing the function of CcpA.

According to another preferred embodiment, the process of the invention comprises preparing a food product having an improved texture and flavor by fermenting a food substrate with a strain of L. casei having a mutation impairing the function of EI.

The invention also provides fermented food products obtainable by the process of the invention, and, in particular fermented food products comprising at least a mutant strain of L. casei as defined above.

The present invention will be further illustrated by the additional description which follows, which refers to examples of construction and use of mutant strains of L. casei of the invention. It should be understood however that these examples are given only by way of illustration of the invention and do not constitute in any way a limitation thereof.

EXAMPLE 1

Characterisation of L. casei ptsH and ptsI Genes

Strains, Plasmids and Culture Conditions

The L. casei strains and plasmids used for the characterisation of ptsH and ptsI genes and construction of mutants thereof are listed in Table 1a and 1b below.

TABLE 1a

| STRAIN (L. casei) | GENOTYPE | ORIGIN |
| --- | --- | --- |
| BL23 | wild-type | Bruce Chassy |
| BL30 | man | (VEYRAT et al., 1994) |
| BL71 | ccpA | (MONEDERO et al., 1997) |
| BL72 | man ccpA | (GOSALBES et al., 1997) |
| BL121 | ptsH1 (S46AHPr) | This work |
| BL122 | ptsH2 (S46THPr) | This work |
| BL123 | ptsH3 (I47THPr) | This work |
| BL124 | ptsI: pVME800 | This work |
| BL126 | ptsI1 (frameshift introduced into the first EcoRI site of ptsI) | This work |

TABLE 1b

| PLASMID | PROPERTIES | ORIGIN |
| --- | --- | --- |
| pUC18 | | PHARMACIA-BIOTECH |
| pRV300 | pBluescript SK- with the pAMβ1 EmR gene | (LELOUP et al., 1997) |
| pUCR-HI | pUC18 with 1.6 kb PCR fragment with part of ptsH and ptsI | This work |
| pVME800 | pRV300 with a 865 bp EcoRI internal ptsI fragment | This work |
| pVMS1 | pRV300 with 9 kb fragment downstream from ptsI | This work |
| pVMH1 | pRV300 with part of ptsI, complete ptsH and 105 bp upstream from ptsH | This work |
| pVMH2 | pVMH1 derivative (codon 46 of ptsH is GCT for Ala) | This work |
| pVMH3 | pVMH1 derivative (codon 46 of ptsH is ACT for Thr) | This work |
| pVMH4 | pVMH1 derivative (codon 46 of ptsH is GAT for Asp) | This work |
| pVMH5 | pVMH1 derivative (codon 47 of ptsH is ACC for Thr) | This work |
| pVMR10 | pVMH1 derivative with a frameshift in the first EcoRI site of ptsI. | This work |

L. casei cells were grown at 37° C. under static conditions in MRS medium (OXOID) or MRS fermentation medium (ADSA-MICRO, Scharlau S. A., Barcelona, Spain) containing 0.5% of the indicated carbohydrates.

For diauxic growth experiments, L. casei strains were grown in MRS basal medium containing in 1 l: polypeptone (DIFCO), 10 g; meat extract (DIFCO), 10 g; yeast extract (DIFCO), 5 g; $K_2HPO_4.3H_2O$, 2 g; sodium acetate, 5 g; di-ammonium citrate, 2 g; $MgSO_4$, 0.1 g; $MnSO_4$, 0.05 g and TWEEN 80, 1 ml. The basal medium was supplemented with different sugars at a final concentration of 0.5%, but for the diauxic growth experiments the sugar concentrations were changed as indicated in the text. *E. coli* DH5α was grown with shaking at 37° C. in Luria-Bertani (LB) medium. Transformed bacteria were plated on the respective solid media containing 1.5% agar. The concentrations of antibiotics used for the selection of *E. coli* transformants were 100 µg per ml ampicillin, and 300 µg per ml erythromycin and for the selection of *L. casei* integrants 5 µg per ml erythromycin. The sugar utilization pattern of certain strains was determined with the API50-CH galeries (BIOMERIEUX, Marcy l'Etoile, France).

TWEEN 80 as described herein is polyoxyethylene sorbitan monooleate.

Purification of HPr

Cells from an over-night culture (1 l of MRS medium) were centrifuged and washed twice with 20 mM Tris-HCl, pH 7.4. The cells were resuspended in 20 mM ammonium bicarbonate buffer, pH 8 (2 ml per gram of cell pellet), sonicated (BRANSON SONIFIER 250) and then centrifuged to remove the cell debris. As HPr resists to heat treatment, the supernatant was kept at 70° C. for 5 min to precipitate most of the other proteins. An additional centrifugation step was performed to remove the heat-denatured proteins. The supernatant was loaded on a SEPHADEX (cross-linked dextran gel) G-75 column (42 cm×1.6 cm) equilibrated with 20 mM ammonium bicarbonate, pH 8, which was eluted with the same buffer, and fractions of 1.5 ml were collected. To test for the presence of HPr in these fractions, a mutant complementation assay with the *S. aureus* ptsH mutant strain S797A was carried out [HENGSTENBERG et al., J. Bacteriol., 99, 383-388, (1969)]. HPr activity was detected in fractions 48 to 56. These fractions were pooled and concentrated to a final volume of 500 µl.

Half of the partially purified HPr was separated by reverse phase chromatography on a VYDAC C-18 HPLC column (300 Å, 250 mm×4.6 mm; TOUZART ET MATIGNON, France). Solvent A was an aqueous solution of 0.1% (v/v) of trifluoroacetic acid and solvent B contained 80% acetonitrile and 0.04% trifluoroacetic acid. Proteins were eluted with a linear gradient from 5 to 100% of solvent B in 60 min at a flow rate of 500 µl/min. Fractions with a volume of about 500 µl were collected manually. The presence of HPr in the fractions was tested by a PEP-dependent phosphorylation assay containing 10 mM $MgCl_2$, 50 mM Tris-HCl, pH 7.4, 10 µl aliquots of the fractions, 10 µM [$^{32}$P]PEP and 1.5 µg of *B. subtilis* enzyme I(His)$_6$. Enzyme I(His)$_6$ and HPr(His)$_6$ of *B. subtilis* were purified by ion chelate chromatography on a Ni-NTA SEPHAROSE column (QIAGEN) after expression from plasmids pAG3 and pAG2, respectively [GALINIER et al., Proc Natl Acad Sci USA 94, 8439-8444, (1997)]. HPr (His)$_6$ from *B. subtilis* was used as a standard in the phosphorylation reactions. [$^{32}$P]PEP was prepared from γ-[$^{32}$P]ATP via the pyruvate kinase exchange reaction [ROOSSIEN et al., Biochim. Biophys. Acta., 760, 185-187, (1983)]. The assay mixtures were incubated 10 minutes at 37° C. and separated on 15% polyacrylamide gels containing 1% SDS [LAEMMLI, Nature, 227, 680-685, (1970)]. After drying the gels, radiolabelled proteins were detected by autoradiography. HPr was found to elute at 60% acetonitrile in fractions 44 to 46. These fractions were pooled, lyophilised and aliquots corresponding to approximately 0.5 nmol of HPr were used to determine the first 21 N-terminal amino-acids of HPr by automated Edman degradation on a 473A APPLIED BIOSYSTEMS microsequencer.

SEPHAROSE is a crosslinked, beaded-form of a polysaccharide polymer material extracted from seaweed.

Cloning of PCR-Amplified *L. casei* ptsHI Fragments.

To amplify *L. casei* DNA fragments containing ptsH and part of ptsI, the following degenerate oligonucleotides were designed based on the N-terminal sequence of HPr and on strongly conserved regions in enzyme I which were detected by carrying out an alignment of different enzyme I sequences:

PTS-H2

(SEQ ID NO: 4)
(5'-ATG GAA AAR CGN GAR TTY AAY-3')

(SEQ ID NO: 19)
(MEKREFN);

PTS-I3

(SEQ ID NO: 5)
(5'-GCC ATN GTR TAY TGR ATY ARR TCR TT-3')

(SEQ ID NO: 20)
(NDLIQYTMA);

PTS-I4

(SEQ ID NO: 6)
(5'-CCR TCN SAN GCN GCR ATN CC-3')

(SEQ ID NO: 21)
(GIAASDG);

where R stands for A or G, Y for C or T, S for C or G and N for any nucleotide. Shown underlined in parentheses are the N-terminal amino acid sequence of HPr and the conserved enzyme I sequences which served to design the primers.

PCR amplification of the two fragments comprising part of the ptsHI operon, was performed with a PROGENE thermocycler (REAL, S. L., Valencia, Spain) programmed for 30 cycles including the following three steps: 30 sec at 95° C., 30 sec at 50° C. and 1 min at 72° C., followed by a final extension cycle at 72° C. for 5 min.

Two combinations of primers (PTS-H2/PTS-I3 and PTS-H2/PTS-I4) gave PCR-amplified fragments of 1.6 kb and 0.3 kb, respectively. Sequencing of the PCR products revealed that the deduced amino acid sequences exhibited strong similarity to the sequences of known enzyme I and HPr. As expected, both DNA fragments began with the 5' end of ptsH and extended to the region in ptsI encoding the conserved sequence chosen as basis for the second primer. The larger of the two fragments obtained with primer PTS-I3 was cloned into pUC18, providing plasmid pUCR-H1. Cloning of PCR fragments was achieved with the SURECLONE Ligation Kit (PHARMACIA BIOTECH, Ltd., Uppsala, Sweden).

A 865 bp EcoRI fragment which contained an internal part of the ptsI gene was obtained from plasmid pUCR-H1 and subcloned into the suicide vector pRV300 [LELOUP et al., Appl. Environm. Microbiol., 63, 2117-2123, (1997)], providing plasmid pVME800.

This plasmid was used to transform the *L. casei* wild-type strain BL23 and integration of the plasmid at the correct location (ptsI::pVME800) was verified by PCR and southern blot.

Restriction analysis of the ptsHI region was carried out by southern hybridisation using DNA isolated from one integrant (BL124) with the aim to identify restriction enzymes allowing cloning of the ptsH and ptsI genes together with their flanking regions.

Cloning of the regions flanking the insertion site of plasmid pRV300 was performed as follows: DNA (10 µg) from *L. casei* BL124 was digested with SacI or HindIII, diluted 500-fold, religated with T4 DNA ligase and different aliquots were used to transform *E. coli* DH5α. Plasmid DNA was isolated from several transformants and subsequently sequenced.

Digestion of BL124 DNA with SacI and religation of the obtained DNA fragments allowed to isolate plasmid pVMS1 carrying an about 9 kb insert. Partial sequencing of this insert revealed that it contained the 3' part of ptsI and its downstream region. The same experiment carried out with HindIII allowed to isolate plasmid pVMH1 carrying a 2.4 kb insert comprising the complete ptsH gene together with part of its promoter region and the 5' part of ptsI.

The sequence containing the complete ptsH promoter and 560 bp of the upstream region was subsequently obtained by reverse PCR. For this purpose, DNA isolated from the L. casei wild-type strain BL23 was cut with PstI and religated with T4 DNA ligase (GIBCO-BRL). 20 ng of the ligated DNA and two primers derived from the 5' part of ptsH and oriented in opposite directions were used to specifically amplify by PCR a 2.3 kb fragment containing the upstream region of ptsH. The sequence comprising 560 bp upstream from the ptsHI promoter has been determined in this fragment.

In total, a continuous stretch of 4150 bp has been sequenced. It contained the complete ptsH and ptsI genes and an open reading frame (ORF) located downstream of ptsI. The stop codon of ptsH was found to overlap with the initiation codon of ptsI by 1 bp, suggesting that these two genes are organised in an operon. Whereas the encoded L. casei HPr and enzyme I exhibited sequence similarities ranging from 65 to 85% when compared to their homologues in B. subtilis, Lactococcus lactis, Lactobacillus sakei, Streptococcus salivarius or Enterococcus faecalis, the protein encoded by the ORF located downstream of ptsI exhibited similarity to the sugar permeases XylE [DAVIS and HENDERSON, J. Biol. Chem., 262, 13928-13932, (1987)] and GalP [PAO et al., Microbiol. Mol. Biol. Rev., 62, 1-34, (1998)] from Escherichia coli. No ORF could be detected in the 560 bp region upstream from the ptsHI promoter.

FIG. 1 is a schematic representation of the sequenced chromosomal L. casei DNA fragment containing the ptsHI operon. Indicated are the three ORF's detected in this fragment, the promoter and terminator of the ptsHI operon and several important restriction sites. The initially isolated PCR fragments H2/I4 and H2/I3 (flanked by inverted arrows) and the 865 bp EcoRI fragment, which was called E800 and subcloned into pRV300, are shown above the schematic presentation of the total DNA fragment.

Transcriptional Analysis of the L. casei ptsHI Operon

To determine the size of the ptsHI transcripts and to test the effect of a man (prevents the uptake of glucose via the PTS) and a ccpA mutation on ptsHI expression, Northern blots were performed with RNA isolated not only from the L. casei wild-type BL23, but also from the mutant strains BL30 (man) [VEYRAT et al., Microbiology, 140, 1141-1149, (1994)], BL71 (ccpA) [MONEDERO et al., J. Bacteriol., 179, 6657-6664, (1997)] and BL72 (man ccpA) [GOSALBES et al., FEMS Microbiol. Lett., 148, 83-89, (1997)], which were grown in medium containing either glucose, lactose or ribose.

L. casei strains were grown in MRS fermentation medium supplemented with 0.5% of the different sugars to an OD at 550 nm between 0.8 and 1. Cells from a 10 ml culture were collected by centrifugation, washed with 50 mM EDTA and resuspended in 1 ml of TRIZOL (phenol-chloroform reagent) (GIBCO BRL). 1 g of glass beads (diameter 0.1 mm) was added and the cells were broken by shaking the cell suspension in a FASTPREP apparatus (BIOSPEC, Bartlesville, Okla., USA) two times for 45 s. RNA was isolated according to the procedure recommended by the manufacturer of TRIZOL, separated by formaldehyde-agarose gel electrophoresis and transferred to HYBOND-N membranes (AMERSHAM).

Hybridisation experiments were carried out with either ptsH- or ptsI-specific probes. With both probes, a mRNA band of about 2.1 kb could be detected, which is in good agreement with the size expected for the combined ptsH and ptsI genes, confirming that these two genes are organised in an operon and that transcription stops at the stem loop structure located downstream of ptsI.

Densitometric measurement of the hybridising bands in the RNA isolated from cells of the different mutants grown in glucose-, lactose-, or ribose-containing medium showed that expression of the ptsHI operon was moderately induced by glucose in the wild type and ccpA mutant, while this effect was less pronounced in the strains carrying the man mutation.

EXAMPLE 2

Construction and Characterisation of ptsH and ptsI Mutants

I—Construction and Characterisation of ptsI Mutants
Mutant BL124

This mutant results from transformation of L. casei wild-type strain BL23 with plasmid pVME800, as described in Example 1 above.

In contrast to the wild-type strain, this mutant can no longer produce acid from fructose, mannose, mannitol, sorbose, sorbitol, amygdaline, arbutine, salicine, cellobiose, lactose, tagatose, trehalose and turanose. However, it can still metabolise ribose, galactose, glucose, N-acetylglucosamine, aesculine, maltose and gluconate, suggesting that in L. casei PTS-independent transport systems exist for this second class of sugars.

Mutant BL126

Plasmid pVMH1 was partially digested with EcoRI and made blunt end (filled in with the Klenow fragment) before it was religated and used to transform E. coli DH5α. From one of the resulting transformants, a plasmid (pVMR10) could be isolated bearing a frame-shift mutation at the EcoRI site located at nucleotide 327 of the ptsI gene, as was confirmed by restriction analysis and DNA sequencing (insertion of 4 additional base pairs). Plasmid pVMR10 was subsequently used to transform L. casei BL23 and an erythromycin-resistant ptsI+ integrant resulting from a Campbell-like recombination was isolated.

From this strain, a ptsI mutant (ptsI1, BL126) could be obtained by a second recombination. BL126 was erythromycin-sensitive and exhibited a fermentation pattern identical to that found for the ptsI::pVME800 mutant BL124. Interestingly, no ptsHI mRNA could be detected in BL126 by Northern blot analysis.

II—Construction of ptsH Mutants Altered at Ser-46 or Ile-47

PCR-based site directed mutagenesis was carried out with the L. casei ptsH gene present in plasmid pVMH1 (Table 1) to replace either Ser-46 with alanine, aspartic acid or threonine, or Ile-47 with threonine.

Site-directed mutagenesis was performed in order to replace the codon for Ser-46 of L. casei ptsH with a codon for Ala, Asp or Thr and the codon for Ile-47 with a codon for Thr.

For this purpose, PCR amplification was carried out using as template the plasmid pVMH1 containing the L. casei wild-type pstH gene as well as the 5' part of the ptsI gene and as primers the reverse primer of pBLUESCRIPT (STRATAGENE) and one of the following oligonucleotides:

5'ptsHS46A

```
                                                (SEQ ID NO: 7)
(5'-AAG AGC GTT AAC TTG AAG GCT ATC ATG GGC
G-3');

5'ptsHS46T
                                                (SEQ ID NO: 8)
(5'-AAG AGC GTT AAC TTG AAG ACT ATC ATG GGC
G-3');

5'ptsHS46D
                                                (SEQ ID NO: 9)
(5'-AAG AGC GTT AAC TTG AAG GAT ATC ATG GGC
G-3');

5'ptsHI47T
                                               (SEQ ID NO: 10)
(5'-AAG AGC GTT AAC TTG AAG TCT ACC ATG GGC
G-3').
```

In these oligonucleotides, the codons for Ser-46 or Ile-47 were replaced by the indicated codon (underlined).

The resulting 1.4 kb PCR fragments containing the ptsH alleles (from codon 40) and the 5' part of ptsI were digested with HpaI (the HpaI site present in ptsH before codon 46 is indicated in italics in the above primers) and SacI and used to replace the wild-type 1.4 kb HpaI/SacI fragment in pVMH1.

In order to confirm the presence of the mutations, the sequence of the ptsH alleles was determined in the four constructed plasmids. To eliminate mutations possibly introduced in the ptsI gene by the PCR amplification, the 1.35 kb BalI/SacI fragment from pVMH1 was used to replace the corresponding fragment in each of the four plasmids containing the various ptsH alleles. A unique BalI site is present 27 bp behind codon 46 of *L. casei* ptsH in pVMH1 and the pVMH1 derivatives carrying the different ptsH alleles.

The four resulting plasmids carrying the various ptsH alleles were named pVMH2, pVMH3, pVMH4 and pVMH5, respectively (Table 1), and were used to transform the *L. casei* ptsI mutant BL126.

Figure 2A:
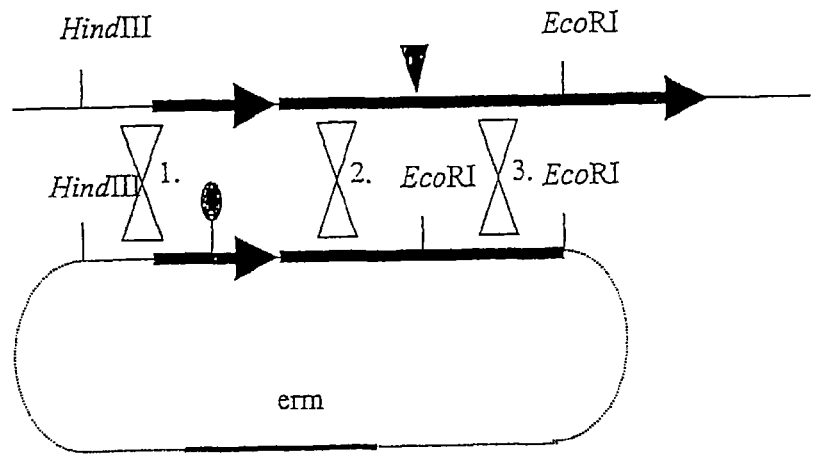
FIG. 2A: Integration of a pVMH plasmid carrying a mutation in ptsH (indicated by the filled circle) into the chromosome of BL126 carrying a frame shift mutation in ptsI (indicated by the filled triangle) by Campbell-like recombination could take place at three different locations (before the ptsH mutation, between the ptsH and ptsI mutations and after the ptsI mutation) resulting in the three different DNA arrangements presented under: "1$^{st}$ recombination" (shown on FIG. 2B).
Figure 2B:
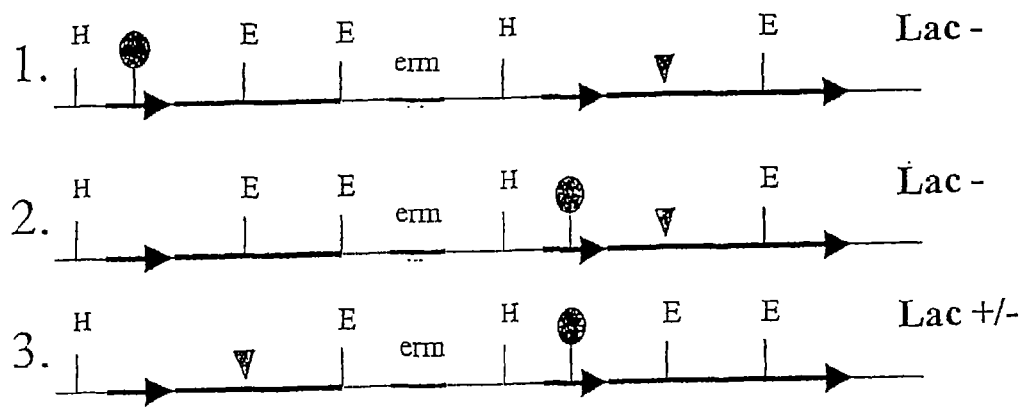
FIG. 2: a schematic presentation of possible recombination events during the construction of ptsH mutants with the ptsI1 strain BL126 and the pVMH plasmids containing the various ptsH alleles.
Figure 2C:
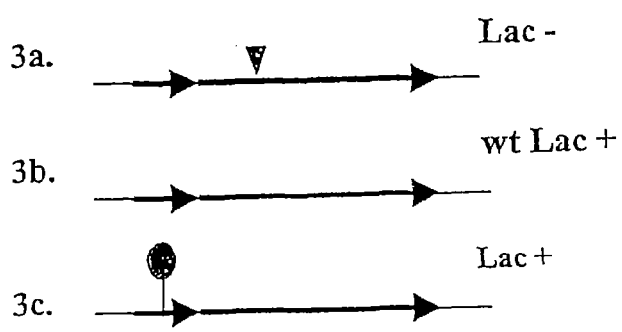

FIG. 2 is a schematic presentation of possible recombination events during the construction of ptsH mutants with the ptsI1 strain BL126 and the pVMH plasmids containing the various ptsH alleles. Integration of a pVMH plasmid carrying a mutation in ptsH (indicated by the filled circle) into the chromosome of BL126 carrying a frame shift mutation in ptsI (indicated by the filled triangle) by Campbell-like recombination could take place at three different locations (before the ptsH mutation, between the ptsH and ptsI mutations and after the ptsI mutation) resulting in the three different DNA arrangements presented under: "1st recombination".

Integrants obtained by the first (1) and second (2) type of recombination exhibited a lac⁻ phenotype, whereas integrants obtained by the third type of recombination (3) could slowly ferment lactose (probably due to a readthrough from a plasmid-located promoter).

The three different DNA arrangements presented on FIG. 2 under: "2nd recombination" are obtained from type 3 integrants after a second recombination event leading to the excision of the pVMH plasmid. 3a provides a lac⁻ strain having a frame shift mutation in ptsI; 3b provides a wild-type strain (lac+); 3c provides the desired ptsH mutant(lac+).

Transformation or the *L. casei* ptsI mutant BL126 with pVMH2, pVMH3, pVMH4 or pVMH5 resulted in erythromycin-resistant recombinants generated by the first recombination.

Type 3 integrants obtained with each of the three pVMH plasmids were grown for 200 generations without selective pressure to allow the second recombination leading to the excision of the pVMH plasmids. Erythromycin-sensitive clones able to ferment lactose were therefore isolated.

Two types of erythromycin-sensitive lactose-fermenting recombinants were obtained which exhibited slightly different growth characteristics. Using appropriate primers, the ptsH alleles of two clones of the slower and faster growing recombinants were amplified by PCR and sequenced. For each ptsH allele, the two faster growing clones contained the wild-type ptsH, whereas the slightly slower growing strains carried either the Ser-46-Ala (ptsH1, BL121), the Ser-46-Thr (ptsH2, BL122) or the Ile-47-Thr ptsH mutation (ptsH3, BL123).

No strain synthesising Ser-46-Asp mutant HPr could be obtained with this method, although PCR amplification followed by DNA sequencing was carried out with fifteen erythromycin-sensitive clones constructed with plasmid pVMH4.

The ptsH Mutations Affect CCR and Diauxic Growth

In order to test the effect of the different amino acid substitutions in HPr on diauxie, the growth behaviour of the mutants on basal MRS broth supplemented with 0.1% glucose and 0.2% lactose was compared to that of the wild-type and a ccpA mutant.

Figure 3:
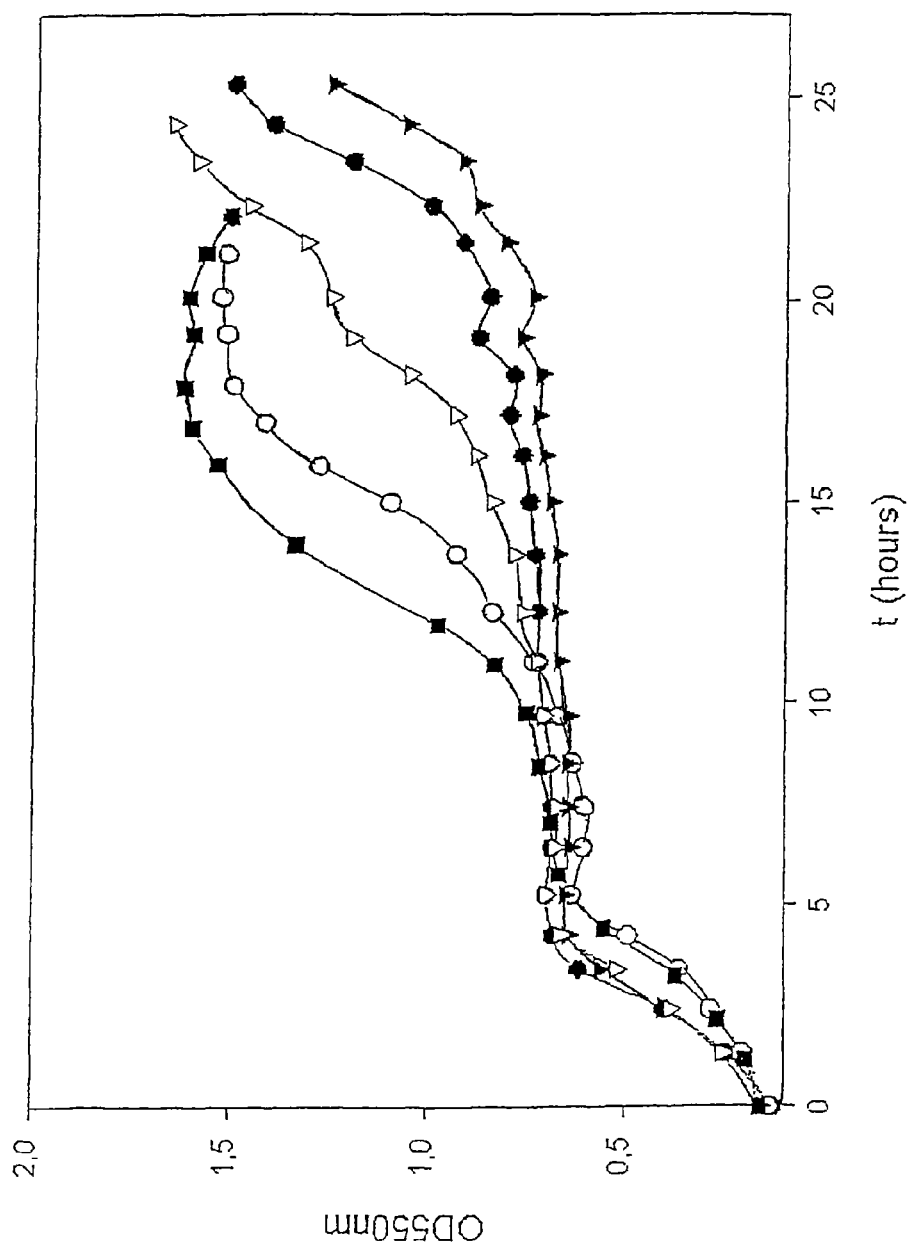
FIG. 3: represents the growth behaviour of *L. casei* wild-type and ccpA and ptsH mutant strains in MRS basal medium containing 0.1% glucose and 0.2% lactose. The symbols represent: filled circles, wild-type BL23; filled squares, ccpA mutant BL71; open circles, ptsH1 mutant BL121; filled triangles, ptsH2 mutant BL122; open triangles, ptsH3 mutant BL123.

FIG. 3 represents the growth behaviour of *L. casei* wild-type and ccpA and ptsH mutant strains in MRS basal medium containing 0.1% glucose and 0.2% lactose. The symbols represent: filled circles, wild-type BL23; filled squares, ccpA mutant BL71; open circles, ptsH1 mutant BL121; filled triangles, ptsH2 mutant BL122; open triangles, ptsH3 mutant BL123.

As previously demonstrated [VEYRAT et al., Microbiology, 140, 1141-1149, (1994); GOSALBES et al., FEMS Microbiol. Lett., 148, 83-89, (1997); GOSALBES et al., J. Bacteriol., 181, 3928-3934, (1999)], the *L. casei* wild-type strain exhibited strong diauxic growth in the presence of these two sugars with a lag phase of about 15 h separating the growth phases on glucose and lactose, whereas in the ccpA mutant strain this lag phase was reduced to 5 h. The diauxic growth observed with the ptsHS46T mutant was very similar to that of the wild-type strain. By contrast, the lag phase was only about 6 h for the ptsHS46A mutant and in between wild-type and ptsHS46A mutant for the ptsHI47T (10 h).

A similar gradation was found when the relief from glucose-mediated repression of N-acetyglucosaminidase activity was investigated.

For the N-acetylglucosaminidase assays, permeabilized *L. casei* cells were prepared following a previously described method [CHASSY and THOMPSON, J. Bacteriol., 154, 1195-1203, (1983)]. The N-acetyl-glucosaminidase assays were carried out at 37° C. in a volume of 250 µl containing 10 mM potassium phosphate, pH 6.8, 1 mM MgCl$_2$, 5 mM p-nitrophenyl N-acetyl-β-D-glucosaminide (SIGMA) and 5 µl of permeabilized cells. The reaction was stopped with 250 µl of 5% Na$_2$CO$_3$ and the OD$_{420}$ was measured. Protein concentrations were determined with the BIO-RAD dye-binding assay.

Figure 4:
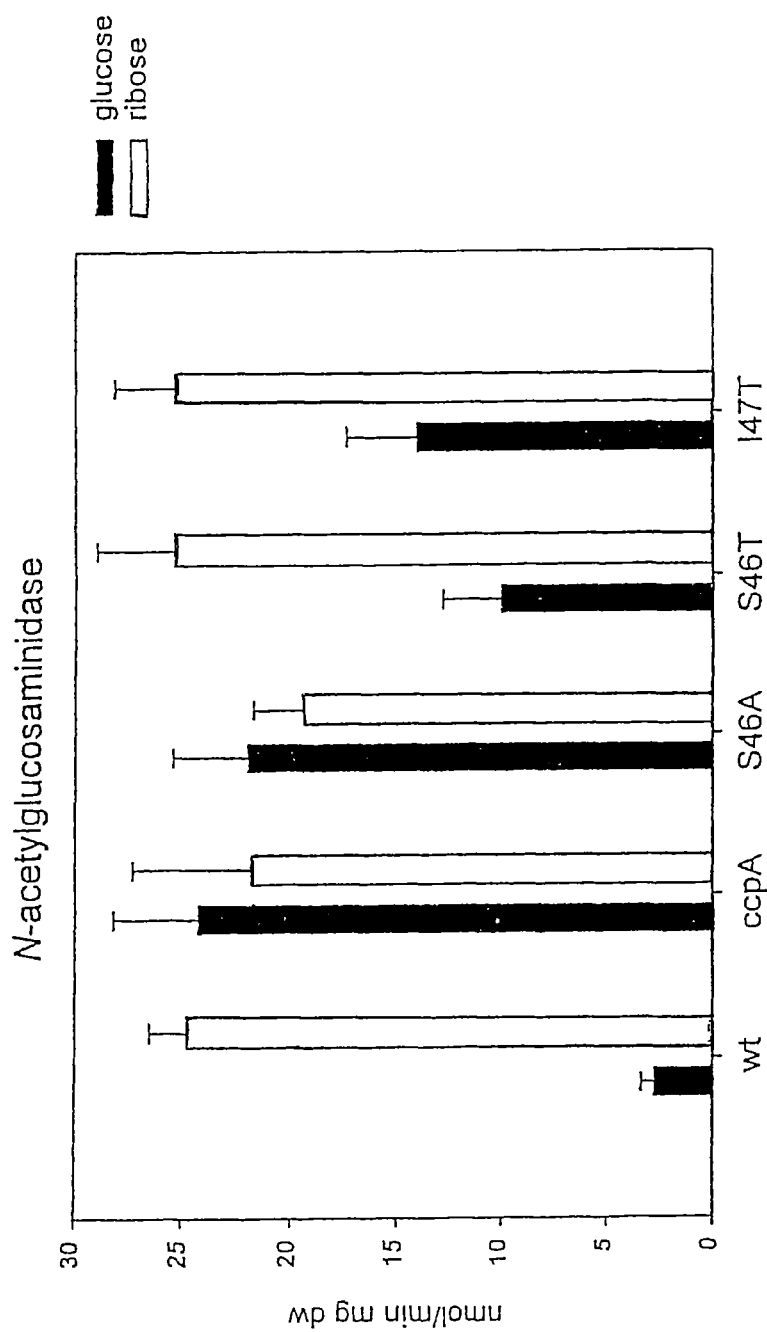
FIG. 4: shows the effect of the various ptsH mutations on CCR of N-acetylglucosaminidase. The N-acetylglucosaminidase activities expressed in nmoles of product formed per min and mg of protein and determined in the *L. casei* wild-type (wt) and the ccpA, ptsH1 (S46A), ptsH2 (S46T) and ptsH3 (I47T) mutant strains grown in MRS basal medium containing 0.5% glucose or ribose are presented.

FIG. 4 shows the effect of the various ptsH mutations on CCR of N-acetylglucosaminidase. The N-acetylglucosaminidase activities expressed in nmoles of product formed per min and mg of protein and determined in the *L. casei* wild-type (wt) and the ccpA, ptsH1 (S46A), ptsH2 (S46T) and ptsH3 (I47T) mutant strains grown in MRS basal medium containing 0.5% glucose or ribose are presented.

Whereas high activity of this enzyme could be measured in ribose-grown wild-type cells, glucose was found to inhibit its activity about 10-fold. Similar as in the ccpA mutant, the repressive effect of glucose on N-acetylglucosaminidase had completely disappeared in the ptsHS46A mutant. Inhibition of N-acetylglucosaminidase activity by the presence of glucose in the growth medium was also clearly diminished in the two other ptsH mutants (about 2-fold inhibition in the ptsHI47T mutant and 2.5-fold inhibition in the ptsHS46T mutant), confirming the importance of Ser-46 phosphorylation of HPr and of the amino acids in the vicinity of Ser-46 for CCR in L. casei.

Therefore, these two tests indicated that there was a remarkable and progressive loss of catabolite repression in the different mutants: wild-type<ptsH2<ptsH3<ptsH1<ccpA.

The ptsH Mutations Affect Inducer Exclusion in L. casei

When L. casei wild-type cells were grown in a medium containing glucose and either ribose or maltose, a diauxic growth behaviour similar to that obtained with cells growing in the presence of glucose and lactose was observed. However, whereas the lag time of the diauxic growth in the presence of glucose and lactose was not or only partly reduced in the ptsH mutants, the diauxic growth completely disappeared when the ptsH strains were grown in a medium containing glucose and either maltose or ribose. These results suggested that phosphorylation of HPr at Ser-46 plays an important role in regulation of the utilization of these two non-PTS sugars by L. casei.

In order to distinguish whether this effect was mediated via interaction of the CcpA/P-Ser-HPr complex with cre sequences or via interaction of P-Ser-HPr with a sugar permease according to the proposed mechanism of inducer exclusion [YE et al., Proc. Natl. Acad. Sci. USA, 91, 3102-3106, (1994); YE et al., J. Bacteriol., 176, 3484-3492, (1994); YE and SAIER, Proc. Natl. Acad. Sci. USA, 92, 417-421, (1995); YE and SAIER, J. Bacteriol., 177, 1900-1902, (1995)], sugar transport experiments were performed.

Cells were grown to mid-exponential phase in MRS fermentation broth containing 0.5% of the indicated sugars. Subsequently, glucose was added to a final concentration of 0.5% and cells were grown for a further 30 min to allow the synthesis of the glucose-specific PTS transport proteins. Cells were washed twice with 50 mM sodium phosphate buffer, pH 7, containing 10 mM $MgCl_2$ and resuspended in 50 mM Tris-maleate buffer, pH 7.2, containing 5 mM $MgCl_2$. Transport assays were carried out in 1 ml of this latter buffer containing 1% peptone and 0.6 mg of cells (dry weight). Samples were preincubated for 5 min at 37° C. prior to adding [$^{14}$C]-labelled sugars (0.5 mCi/mmol, ISOTOPCHIM, Ganagobie-Peyruis, France) to a final concentration of 1 mM. Samples of 100 µl were withdrawn at different time intervals, rapidly filtered through 0.45 µm pore-size filters, washed twice with 5 ml of cold Tris-maleate buffer and the radioactivity retained was determined by liquid scintillation counting.

FIG. 5 shows the effect of glucose and 2-deoxy-D-glucose on maltose and ribose uptake by wild-type and ptsH mutant cells. Ribose transport by the L. casei wild-type strain BL23 was measured in the absence and presence of glucose and 2-deoxy-D-glucose (A). Maltose transport in the absence and presence of glucose or 2-deoxy-D-glucose was determined in the L. casei wild-type strain BL23 (B), the ptsH1 mutant BL121 (C), the ptsH2 mutant BL122 (D), the ptsH3 mutant BL123 (E) and the ptsI mutant BL126 (F). The symbols represent: squares, ribose or maltose uptake in the absence of other sugars; diamonds, ribose or maltose uptake with glucose (10 mM final concentration) added after 10 or 4 min, respectively; circles, ribose or maltose uptake with 2-deoxy-D-glucose (10 mM final concentration) added after 10 or 4 min, respectively; triangles, the cells were incubated for 10 min in the presence of 20 mM glucose before the maltose uptake reaction was started.

Figures 5A, 5B:
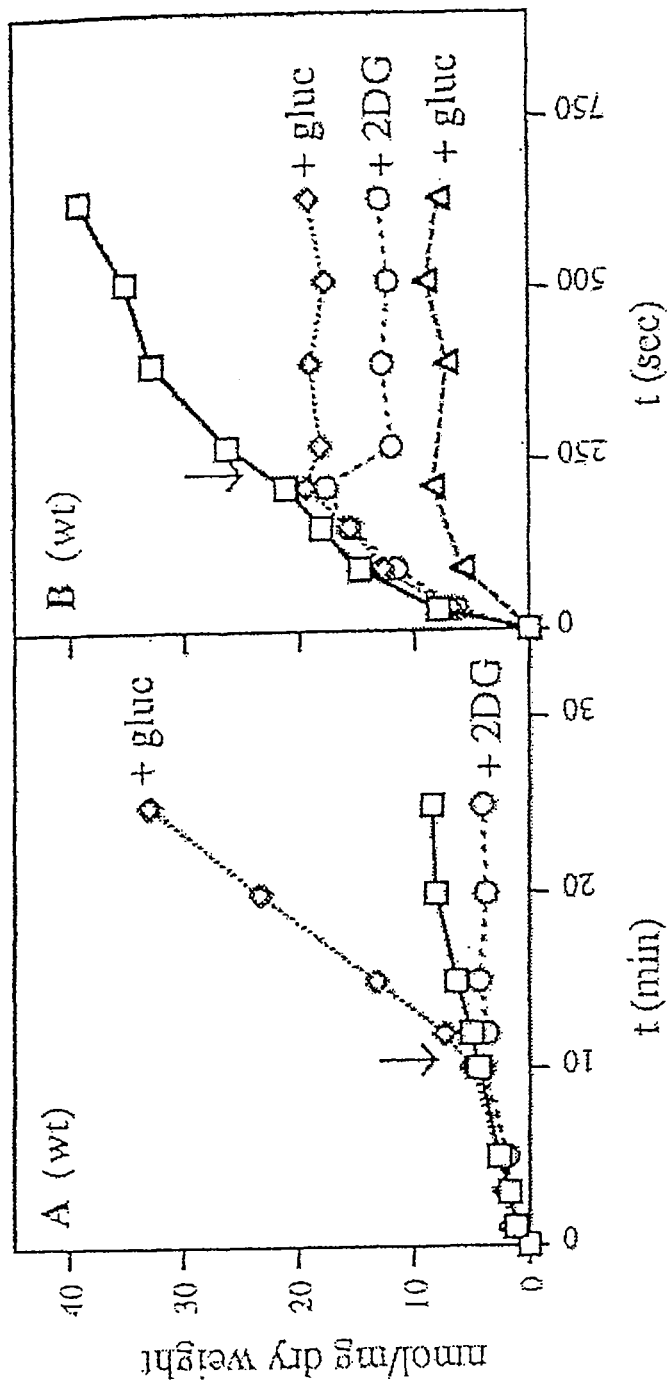
FIG. 5A-5F: shows the effect of glucose and 2-deoxy-D-glucose on maltose and ribose uptake by wild-type and ptsH mutant cells. Ribose transport by the *L. casei* wild-type strain BL23 was measured in the absence and presence of glucose and 2-deoxy-D-glucose (A). Maltose transport in the absence and presence of glucose or 2-deoxy-D-glucose was determined in the *L. casei* wild-type strain BL23 (B), the ptsH1 mutant BL121 (C), the ptsH2 mutant BL122 (D), the ptsH3 mutant BL123 (E) and the ptsI mutant BL126 (F). The symbols represent: squares, ribose or maltose uptake in the absence of other sugars; diamonds, ribose or maltose uptake with glucose (10 mM final concentration) added after 10 or 4 min, respectively; circles, ribose or maltose uptake with 2-deoxy-D-glucose (10 mM final concentration) added after 10 or 4 min, respectively; triangles, the cells were incubated for 10 min in the presence of 20 mM glucose before the maltose uptake reaction was started.

The uptake of ribose by ribose-grown L. casei wild-type cells is shown in FIG. 5A. The addition of glucose to ribose-transporting wild-type cells caused no inhibition of ribose uptake but instead increased the transport about four-fold. The addition of the glucose analogue 2-deoxy-D-glucose completely abolished ribose uptake. It is most likely that the depletion of energy caused by the transport and accumulation of the non-metabolizable glucose analogue is responsible for the inhibitory effect of 2-deoxy-D-glucose on ribose transport.

Figures 5C, 5D:
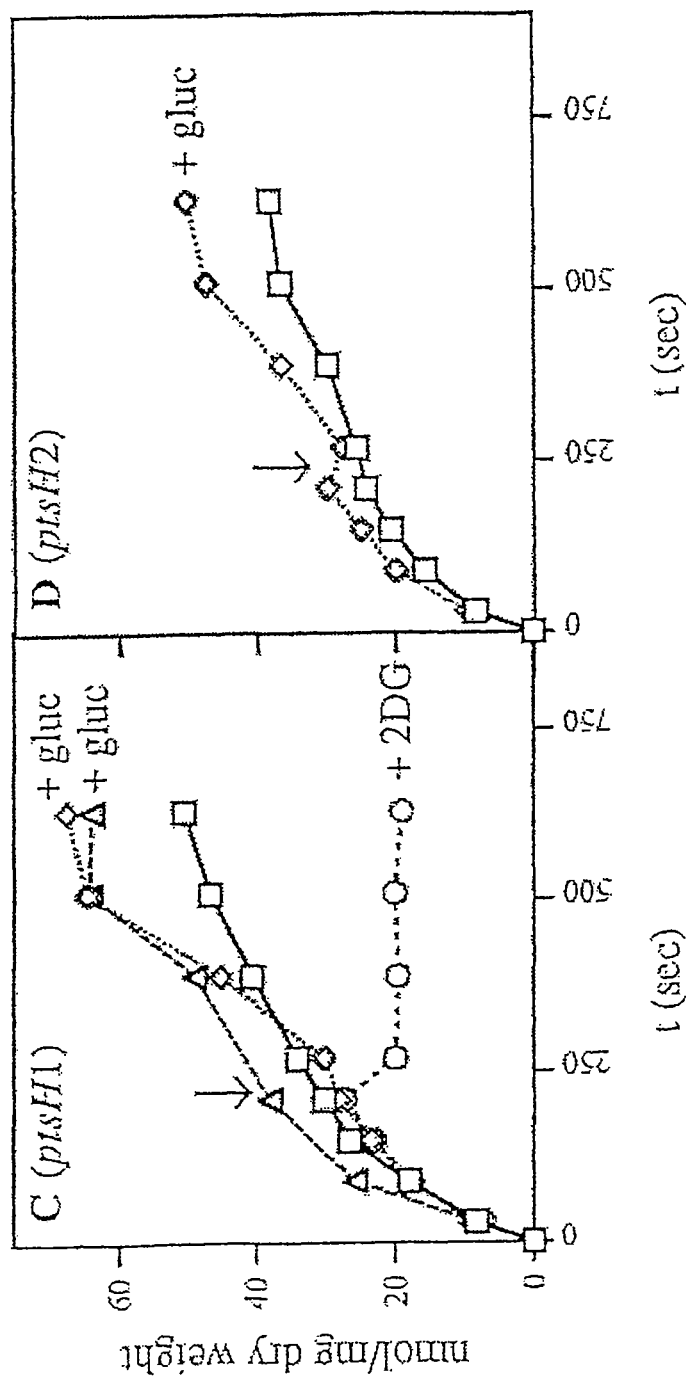
Figures 5E, 5F:
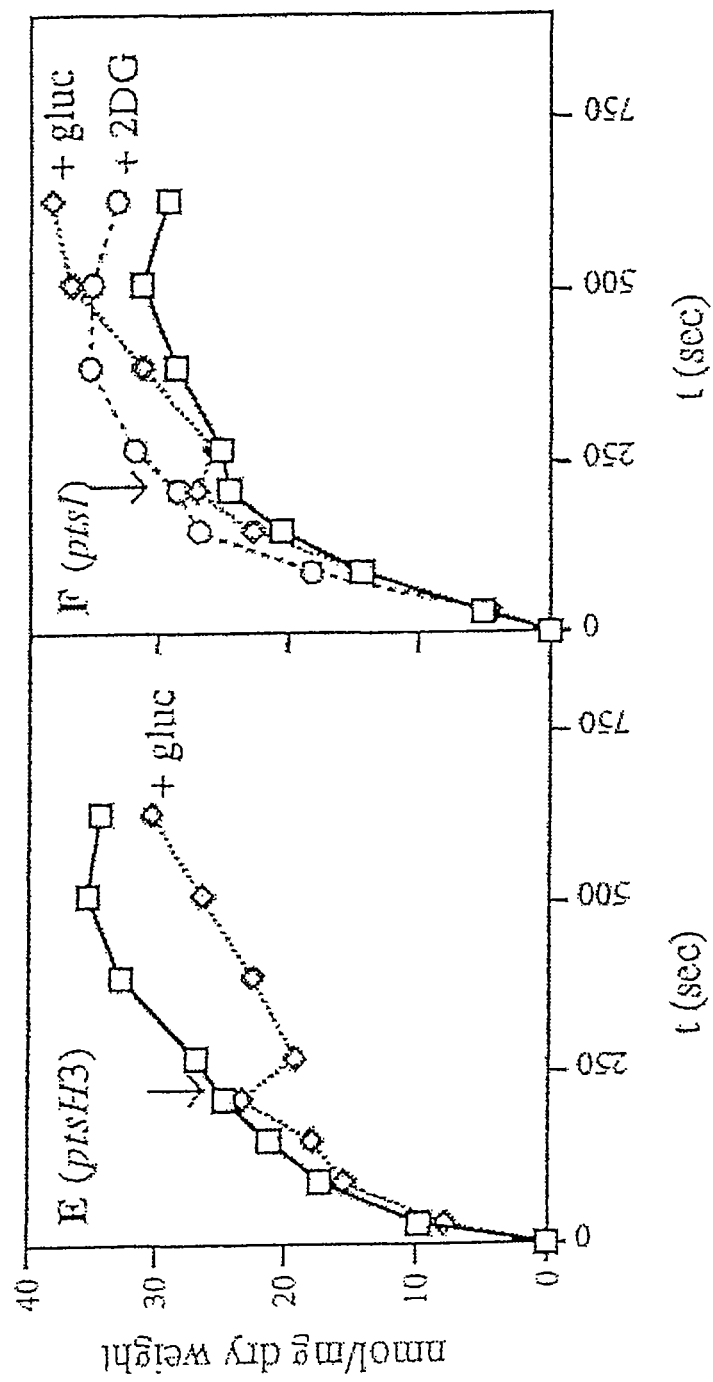

In contrast to the stimulatory effect exerted by glucose on ribose uptake, maltose transport was found to be instantaneously arrested when glucose or 2-deoxyglucose was added to L. casei wild-type cells transporting maltose. Maltose uptake was also completely abolished when glucose or 2-deoxyglucose was added to the cell suspension 10 minutes before the addition of maltose (FIG. 5B). The ptsH1 (S46AHPr) mutant showed a completely different behaviour to the wild type strain (FIG. 5C). Maltose uptake in this strain was slightly higher, and the addition of glucose caused a further increase of the maltose transport rate. A similar, but less pronounced stimulatory effect of glucose on maltose transport was found for the ptsH2 (S46THPr) mutant (FIG. 5D), whereas no change of the maltose transport rate following glucose addition was observed for the ptsH3 (I47THPr) mutant (FIG. 5E). In the ptsI mutant BL126, which is unable to transport glucose and 2-deoxy-D-glucose via the PTS, the presence of glucose exerted no inhibitory effect on maltose uptake (FIG. 5F).

The measure of glucose uptake in the ptsI mutant BL126 shows that glucose is transported 10-times slower than the wild-type strain (data not shown). A slower glucose uptake and metabolism is most likely responsible for the failure of glucose to elicit inducer exclusion in the ptsI mutant strain. By contrast, in a ccpA mutant strain, glucose exerts an inhibitory effect on maltose uptake identical to that observed with the wild-type strain. This result clearly establishes that CcpA is not involved in glucose-triggered maltose exclusion.

To make sure that growing the cells for 30 min in glucose-containing medium had no drastic effect on expression of the maltose genes, inducer exclusion experiments were carried out with cells which had not been exposed to glucose. Under these conditions, addition of glucose to maltose transporting cells exerts a strong inhibitory effect on maltose uptake in the wild-type and ccpA mutant strains, although maltose continues to be slowly taken up by these cells after the addition of glucose. By contrast, the presence of glucose completely arrests maltose uptake by cells which have been grown on glucose for 30 min. However, with the ptsH1, ptsH2 and ptsH3 mutants grown only on maltose, glucose exerts no inhibitory effect at all on maltose uptake, clearly establishing that the failure of glucose to inhibit maltose transport in the ptsH mutant strains is not related to pregrowing the cells in glucose-containing medium.

The observed inhibition of maltose transport could have been due to elevated secretion of maltose fermentation products when glucose was added to wild-type cells. In the ptsH mutants, this glucose effect might have been less pronounced. To exclude this possibility, we also measured sugar consumption by resting cells which had been grown on maltose and for the last 30 min before harvesting the cells on maltose and glucose. In order to follow the sugar consumption by the L. casei wild-type and ptsH1 mutant strains, cells were grown and harvested as described for the transport studies and 18 mg of cells (dry weight) were resuspended in 5 ml of 50 mM sodium phosphate buffer, pH 7. After a 5 min incubation at 37° C., maltose and glucose were added to a final concentration of 0.04 and 0.2%, respectively. Samples of 300 µl were withdrawn at different time intervals, boiled for 10 min and clarified by centrifugation. The sugar content in the supernatant was determined with a coupled spectrophotometric test using α-glucosidase and hexokinase/glucose-6-P dehydrogenase as recommended by the supplier (BOEHRINGER-MANNHEIM, Germany).

FIG. 6 shows maltose consumption by resting cells of the L. casei wild-type strain BL23 and the ptsH1 mutant BL121 in the presence or absence of glucose. The symbols represent: squares, maltose concentration in the medium in experiments without glucose; diamonds, maltose concentration and circles, glucose concentration in the medium when glucose was added three minutes after the experiment had been started.

Figure 6A:
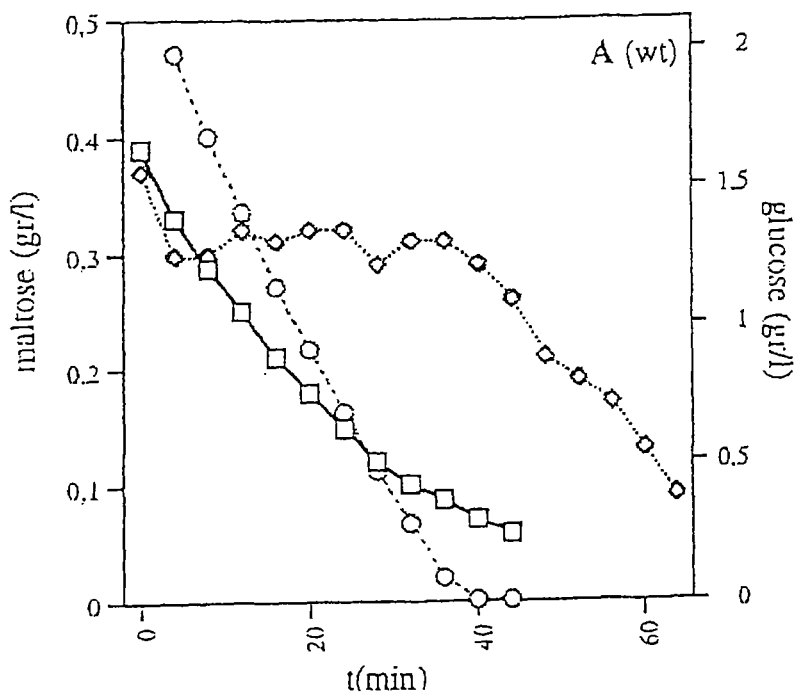
FIG. 6: shows maltose consumption by resting cells of the *L. casei* wild-type strain BL23 and the ptsH1 mutant BL121 in the presence (FIG. 6A) or absence (FIG. 6B) of glucose. The symbols represent: squares, maltose concentration in the medium in experiments without glucose; diamonds, maltose concentration and circles, glucose concentration in the medium when glucose was added three minutes after the experiment had been started.
Figure 6B:
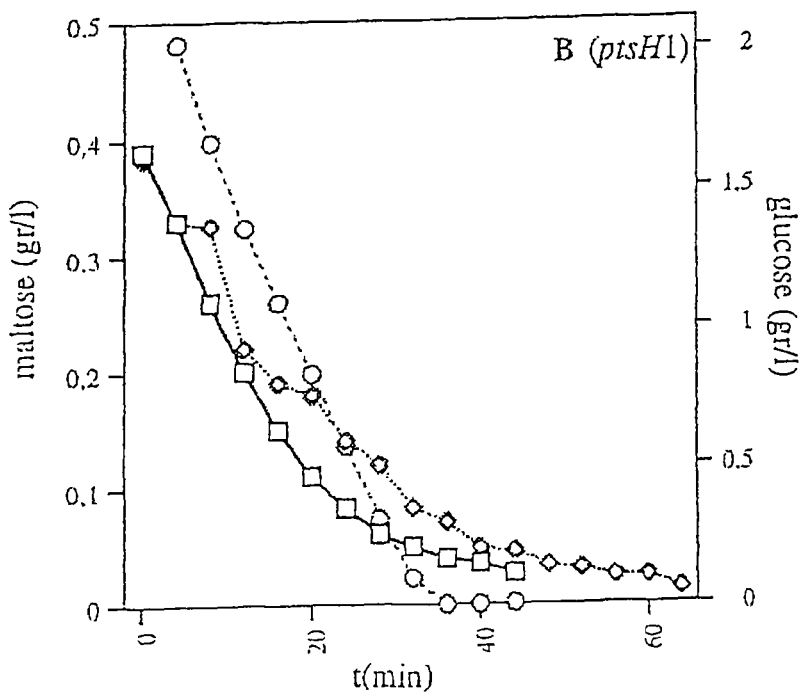

The results presented in FIG. 6A confirm that maltose is not utilised in the presence of glucose by L. casei wild-type cells. Maltose consumption stopped immediately when glucose was added and the maltose concentration remained constant in the medium as long as glucose was present. Maltose consumption re-started only when glucose had completely disappeared from the medium. By contrast, the addition of glucose to ptsH1 mutant cells taking up maltose caused only a short transient inhibition of maltose consumption, which was followed by the simultaneous utilization of both sugars (FIG. 6B). Reduced uptake of glucose by the ptsH1 mutant does not seem to be responsible for the absence of the inhibitory effect of glucose, as in this strain glucose was utilized slightly faster compared to the wild-type strain. These results suggest that phosphorylation of Ser-46 in HPr is necessary for the exclusion of maltose from L. casei cells by glucose and probably other rapidly metabolisable carbon sources and that P-Ser-HPr plays an important role in the regulatory phenomenon called inducer exclusion [YE et al., Proc. Natl. Acad. Sci. USA, 91, 3102-3106, (1994); YE et al., J. Bacteriol., 176, 3484-3492, (1994); YE and SAIER, Proc. Natl. Acad. Sci. USA, 92, 417-421, (1995); YE and SAIER, J. Bacteriol., 177, 1900-1902, 1995)].

EXAMPLE 3

Cloning and Characterisation of L. casei hprK Gene

Strains, Plasmids and Culture Conditions

The L. casei strain ATCC 393, cured of plasmid pLZ15, and the mutant strains ccpA::erm [MONEDERO et al., J. Bacteriol., 179, 6657-6664, (1997)], ptsH1 (Ser46Ala) and ptsH2 (Ser46Thr) were used. Bacteria were grown under static conditions at 37° C. in MRS medium (DIFCO Laboratories, Detroit, Mich.) or MRS fermentation medium (SCHARLAU S. A., Barcelona, Spain). For diauxic growth experiments, L. casei strains were pregrown in an overnight culture of MRS basal medium containing in 1 l: polypeptone, 10 g; meat extract, 10 g; yeast extract, 5 g (all from Difco Laboratories); $K_2HPO_4.3H_2O$, 2 g; sodium acetate, 5 g; dibasic ammonium citrate, 2 g; $MgSO_4$, 0.1 g; $MnSO_4$, 0.05 g, TWEEN 80, 1 ml and glucose, 5 g. The overnight culture was used to inoculate 30 ml fresh basal medium containing 0.05% glucose and either 0.05% lactose or 0.05% maltose at an $OD_{550}$=0.05. the inoculated medium was subsequently incubated at 37° C. Samples of 1 ml were withdrawn at the indicated time intervals to follow growth by measuring the $OD_{550}$.

Escherichia coli NM522 (APPLIGENE ONCOR LIFE-SCREEN, Watford, UK) was grown with shaking at 37° C. in Luria-Bertani (LB) medium. Standard cloning procedures were carried out with E. coli NM522 cells, and transformed bacteria were plated on solid media containing 1.5% agar. The antibiotic concentrations for selecting E. coli transformants were 100 µg per ml ampicillin or 25 µg per ml kanamycin and 5 µg per ml erythromycin for the selection of L. casei integrants.

The plasmids used in this study were pBC KS+ (STRATAGENE, La Jolla, Calif.), pQE30 (QIAGEN, Chatsworth, Calif.) and the integrative vector pRV300.

Cloning of hprK Gene

DNA Amplification by PCR

Polymerase chain reactions (PCR) aimed to obtain fragments of the L. casei hprK gene were carried out with Taq DNA polymerase (APPLIGENE) by using chromosomal L. casei DNA as a template and one of the following pairs of oligonucleotides:

```
i)  ohprKLc1
                                      (SEQ ID NO: 11)
    (5'-GGNRTNGGNAARAGYGARAC-3')

ohprKLc2
                                      (SEQ ID NO: 12)
    (5'-RAARTTNCCCCANCGNCC-3')

ii) ohprKLc3
                                      (SEQ ID NO: 13)
    (5'-ATAAAGCTTGARMTGACNGGNTAYTTYRAYTWYTA-3');

ohprKLc4
                                      (SEQ ID NO: 14)
    (5'-ATTGAAAAGAGCTCGGATTAAGTGCT-3').
``` ohpr KLc3 and ohpr KLc4 contain restriction sites for HindIII and SacI, respectively, which are indicated in italics.

Oligonucleotide ohprKLc4 corresponds to the sequence located 9-35 bp downstream of the hprK stop codon. The C at position 10 of this sequence was replaced with an A and the A in position 12 with a C to allow the creation of the SacI site. To exclude errors introduced by PCR, each DNA fragment was amplified in at least two independent experiments, cloned into pBC KS+ (STRATAGENE) (cut with EcoRV or HindIII and SacI) providing plasmids pHKLc1 and pHKLc2, respectively, and sequenced on a PERKIN ELMER ABIPRISM 373 automated sequencer. The fragment of the hprK gene in pHKLc1 was oriented in the same direction as the lacZ fragment.

By using these two primers and L. casei DNA as a template, a 879 bp fragment could be amplified by PCR. The PCR fragment was cloned into pBC KS+ digested with EcoRV providing plasmid pHKLc1 and the insert was sequenced. Analysis of the sequence data suggested that the PCR fragment encodes the 162 C-terminal amino acids of HprK and the 129 N-terminal amino acids of Lgt.

To obtain part of the missing sequence of the presumed L. casei hprK, a PCR was carried out using L. casei DNA as a template and the oligonucleotides ohprKLc3, and ohprKLc4. The obtained 875 bp PCR fragment was digested with HindIII and SacI and was cloned into pBC KS+ cut with the same enzymes providing plasmid pHKLc2. DNA sequencing and comparison with known HprK sequences suggested that the amplified DNA fragment encodes amino acids 40 to 319 of L. casei HprK.

Construction of a L. casei hprK Mutant and Cloning of the Entire hprK

A point mutation was introduced into the hprK gene of *L. casei* by replacing the leucine-encoding codon 208 (with respect to the complete hprK gene) with an amber codon.

A PCR was carried out using plasmid pHKLc2 as a template and the two oligonucleotides:

```
ohprKLc5
                                      (SEQ ID NO: 15)
(5'-CCCCTCGAGGTCGACGGTATGGATAAGCTTGA-3');
``` which contains part of the multiple cloning site of pHKLc2 including a SalI restriction site (in italics) and a replacement of the C in position 21 by a G (underlined) destroying the ClaI site and:

```
ohprKLc6
                                      (SEQ ID NO: 16)
(5'-CATGACATCGATAATGCCCTAGCCACGAATTTC-3').
```

Oligonucleotide ohprKLc6 is based on the DNA sequence from position 610 to 643 of *L. casei* hprK containing a ClaI site (in italics). In position 20 of ohprKtc6, a T is present instead of an A, changing the leucine-encoding TTG triplet (in position 208 of hprK) to an amber codon (underlined).

The resulting 522 bp PCR fragment was digested with SalI and ClaI and cloned into pHKLc1 cut with the same enzymes, thus providing pHKLc3 containing the 3' part of hprK with the amber mutation and the 5' part of lgt. Plasmid pHKLc3 was digested with HindIII and SacI and the resulting 1312 bp fragment was cloned into the integrative vector pRV300 cut with the same enzymes to give the 4.8 kb plasmid pHKLc208 (Am).

Erythromycin-resistant *L. casei* clones were obtained. In eight clones, the integration of pHKLc208(Am) was tested by Southern blots using as a probe a 590 bp internal hprK fragment. Only one HindIII fragment of 5.2 kb could be detected with DNA from wild-type *L. casei* ATCC 393, whereas seven of the eight erythromycin-resistant clones gave two bands with a size of 3.6 and 6.5 kb (data not shown), suggesting that plasmid pHKLc208(Am), which contains a single HindIII site, had been integrated in the chromosome of these transformants. In the remaining eighth erythromycin-resistant clone, two copies of pHKLc208(Am) seemed to be integrated in tandem, as three fragments of 3.6, 6.5 and 4.8 kb could be detected on the Southern blot.

Campbell-like recombination of pHKLc208(Am) with the *L. casei* chromosome can occur at two different sites with respect to the position of the PCR-introduced amber codon, giving rise to two types of integrants exhibiting either an HprK⁻ or HprK⁺ phenotype.

One of the mutants in which the presence of the hprK208 (Am) mutation has been confirmed by DNA sequencing of appropriate PCR products was named LcG102 and used for further studies. Chromosomal DNA of LcG102 was isolated, digested with HindIII, religated, transformed into *E. coli* NM522 and 3 ampicillin-resistant clones were chosen for further experiments. The plasmids present in the 3 clones were purified and found to carry an about 3.2 kb insert. DNA sequencing of the plasmid pHKLcUS from one of the transformants revealed that the insert contained in addition to the insert of pHKLc208(Am) the 5' part of the presumed hprK, its promoter region and two complete and one incomplete ORF located upstream of hprK (FIG. 1). The proteins encoded by these three ORF's exhibited 23, 22 and 36% sequence identity, respectively, when compared to the proteins encoded by the *B. subtilis* yvlB, yvlC and yvlD genes [KUNST et al., Nature, 390, 249-256, (1997)].

The presumed *L. casei* hprK gene consists of 957 bp and encodes a protein of 35349 Da composed of 319 amino acids, which exhibits 50% sequence identity when compared to *B. subtilis* HprK. As in all other known HprK, the A-motif of nucleotide binding proteins ($GX_4GKS$) is present around position 160. The presumed hprK gene starts with an ATG, which is preceded by a putative ribosome binding site (AA-GAAAGG) located 8 bp upstream of the start codon. Downstream of hprK and separated from hprK by only 1 bp begins the lgt gene. The cloned lgt fragment encodes the first 129 amino acids of *L. casei* Lgt which exhibit 53% sequence identity when compared to the corresponding N-terminal part of *B. subtilis* Lgt.

EXAMPLE 4

Characterisation of Wild Type and Mutant HprK

*L. casei* HprK is a Bifunctional Enzyme Regulated by FBP and $P_i$

In order to confirm that the presumed hprK gene encodes indeed *L. casei* HprK and to test whether it exhibits both HPr kinase and P-Ser-HPr phosphatase activities similar to the *B. subtilis* and *Enterococcus faecalis* enzymes, His-tagged *L. casei* HprK was purified.

To purify *L. casei* HprK carrying a His-tag, PCR amplification was carried out using chromosomal *L. casei* DNA as a template and the two oligonucleotides:

```
                                      (SEQ ID NO: 17)
5'-GTGGGATCCATGGCAGACAGCG-3'
and (SEQ ID NO: 18)
5'-TACGGTACCAATGAACTTCCA-3'
``` containing a BamHI and a KpnI restriction site, respectively (in italics). The resulting 1033 bp fragment containing the complete hprK gene was cut with BamHI and KpnI and cloned into plasmid pQE30 (QIAGEN) cut with the same restriction enzymes to give pQEHKLc. The correct sequence of the amplified hprK was confirmed by DNA sequencing.

In order to purify His-tagged *L. casei* HprK, *E. coli* strain M15[pREP4] (QIAGEN) was transformed with plasmid pQEHKLc. A resulting transformant was isolated and grown in 1 l of LB medium (DIFCO) at 37° C. until it reached an $OD_{595}$ of about 0.7. Subsequently, expression was induced by addition of 1 mM IPTG. Cells were grown for an additional 3 h before they were centrifuged, washed twice with 100 mM Tris-HCl buffer, pH 7.4, and broken by sonication (BRANSON SONIFIER 251). Cell debris was removed by centrifugation and the resulting supernatant was loaded onto a Ni-NTA-agarose column (QIAGEN) equilibrated with buffer A (50 mM Tris-HCl, pH 7.4, 15% glycerol and 50 mM $Na_2SO_4$). After washing with 30 mM imidazole, HprK was eluted with the equilibration buffer containing 300 mM imidazole. HprK-containing fractions were pooled, dialyzed against 50 mM Tris-HCl buffer, pH 7.4, containing 0.1 mM DTT and 0.1 mM PMSF and subsequently stored at −80° C.

His-tagged *B. subtilis* and its seryl-phosphorylated derivative were prepared as described in [GALINIER et al., Proc. Natl. Acad. Sci. USA, 95, 1823-1828, (1998)]. For the preparation of P-Ser-HPr, HPr kinase present in the phosphorylation mixture was inactivated by keeping it for 5 min at 65° C. once the phosphorylation reaction was terminated. To completely remove ATP and FBP from the P-Ser-HPr preparation it was desalted on a 10 ml SEPHADEX G-10 column. His-tagged B. subtilis HprK was overproduced and purified as described in [GALINIER et al., Proc. Natl. Acad. Sci. USA, 95, 1823-1828, (1998)], and B. subtilis Ser-46-Ala mutant HPr was obtained as described in [EISERMANN et al., J. Biol. Chem., 263, 17050-17054, (1998)].

Using HPr(His)$_6$ or P-Ser-HPr(His)$_6$ from B. subtilis as substrates, HprK of L. casei was indeed found to be bifunctional.

The effects of FBP and inorganic phosphate (P$_i$) on HPr kinase and P-Ser-HPr phosphatase activities of purified L. casei HprK(His)$_6$ were measured. The assay mixtures contained in a total volume of 20 µl 0.005, 0.02 or 0.05 µg HprK(His)$_6$, 5 mM MgCl$_2$, 50 mM Tris-Hcl, pH 7.4 and in addition for the kinase assay 2.5 µg B. subtilis P-Ser-Hpr (His)$_6$ and varying concentrations of sodium phosphate and were incubated for 5 min at 37° C. The reactions were stopped by heating the assay mixtures for 5 min at 65° C. Equal volumes of sample buffer were added to the assay mixtures before separating HPr and P-Ser-HPr on a 12.5% non-denaturating polyacrylamide gel.

ATP-dependent HPr phosphorylation was slightly stimulated by FBP at concentrations higher than 1 mM, whereas the P-Ser-HPr phosphatase activity was clearly stimulated by 0.2 mM and higher concentrations of P$_i$. Stimulation of ATP-dependent HPr phosphorylation by FBP was more evident when the HPr kinase assays were carried out in the presence of P$_i$. With 1 mM P$_i$, no HPr phosphorylation could be observed in the absence of FBP, whereas in the presence of 20 mM FBP a strong HPr kinase activity could be detected. When using 8 mM P$_i$, FBP had almost completely lost its stimulating effect on HPr phosphorylation. HprK-catalyzed phosphorylation occurs at Ser-46 of HPr, as B. subtilis Ser-46-Ala mutant HPr was not phosphorylated by the L. casei HprK.

HPr kinase and P-Ser-HPr phosphatase activities were determined in crude extracts of L. casei wild-type and pHKLc208(Am) integrants.

Cells were grown in 10 ml MRS medium, harvested by centrifugation and washed twice with 50 mM Tris-HCl buffer, pH 7.4. The pellet was resuspended in 800 µl of the same buffer, cells were broken by sonication (BRANSON SONIFIER 250) and cell debris was removed by centrifugation.

To demonstrate HPr kinase activity in L. casei crude extracts, ATP-dependent phosphorylation assays were carried out in the presence or absence of 1.5 µg B. subtilis HPr(His)$_6$ in a total volume of 20 µl containing 5 µl crude extract, 25 µM [γ-$^{32}$P]ATP (0.5 µCi), 10 mM MgCl$_2$, 50 mM Tris-HCl, pH 7.4 and 20 mM FBP. The phosphorylation reaction was stopped by adding an equal volume of sample buffer [LAEMMLI, Nature, 227, 680-685, (1970)] to the assay mixtures before loading them onto a 15% polyacrylamide gel containing 0.1% SDS. After electrophoresis, gels were treated for 5 min with boiling 16% trichloroacetic acid before they were dried and exposed to autoradiography (BIOMAX MR, Kodak). Control experiments were carried out with 0.5 µg of purified B. subtilis HprK(His)$_6$ and 1.5 µg HPr(His)$_6$.

No HPr kinase activity was detected in crude extracts of hprK208(Am) mutant strain.

To test whether this mutant was also devoid of P-Ser-HPr phosphatase activity, crude extracts of L. casei wild-type and the hprK208(Am) mutant strain were prepared and their capacity to dephosphorylate P-Ser-HPr was assayed in the presence of 20 mM P$_i$.

P-Ser-HPr phosphatase assays were carried out by incubating a 20 µl assay mixture containing 10 µl crude extract, 2.5 µg B. subtilis P-Ser-HPr(His)$_6$, 20 mM sodium phosphate, pH 7.2, 10 mM MgCl$_2$ and 50 mM Tris-HCl, pH 7.4, for 10 min at 37° C. The dephosphorylation reaction was stopped by heat inactivation at 65° C. for 5 min. An equal volume of sample buffer was added to the assay mixtures before separating HPr and P-Ser-HPr on a 12.5% non-denaturing polyacrylamide gel.

Whereas P-Ser-HPr phosphatase activity could be easily seen with crude extracts of the wild type strain, no activity could be detected with this test in crude extracts of the hprK208(Am) mutant LcG102. Even increasing the incubation time from 10 to 30 min did not allow to detect dephosphorylated HPr in the P-Ser-HPr phosphatase assay with crude extracts of the hprK208(Am) mutant.

The hprK208(Am) Mutation Affects CCR

To determine whether similar to B. subtilis HprK, L. casei HprK is also involved in CCR, the repressive effect of glucose on N-acetylglucosaminidase activity was measured in the hprK208(Am) mutant and compared to the activity found in wild-type and ccpA and ptsH1 mutant strains.

Wild-type and ccpA, ptsH1 and hprK208(Am) mutant cells were grown in 10 ml MRS fermentation medium to an OD$_{595}$ between 0.7 and 0.9, centrifuged and washed twice with 10 mM sodium phosphate buffer, pH 7.2. Permeabilized L. casei cells were obtained as described in [CHASSY et al., J. Bacteriol., 154, 1195-1203, (1983)]. To measure N-acetylglucosaminidase activity, a 500 µl assay mixture containing 10 µl de permeabilized cells, 10 mM sodium phosphate, pH 6.8, 1 mM MgCl$_2$ and 5 mM p-nitrophenyl-N-acetyl-β-D-glucosaminide (SIGMA) was incubated for 10 min at 37° C. The reaction was stopped with 500 µl of 5% Na$_2$CO$_3$, and the OD$_{420}$ was measured.

In the wild-type strain ATCC 393, N-acetylglucosaminidase activity was repressed 18-fold by the presence of glucose, whereas N-acetylglucoaminidase activity was derepressed in ribose-grown cells (Table 2). Similar as in L. casei ccpA or ptsH1 mutants CCR of N-acetylglucosaminidase activity was strongly diminished in the hprK208(Am) mutant LcG102 (Table 2).

TABLE 2

| | N-acetylglucosaminidase activity $^a$ | |
|---|---|---|
| Strains | Glucose | Ribose |
| wild-type | 2.0 ± 0.9 | 37.6 ± 6.7 |
| hprK208(Am) | 26.3 ± 1.7 | 31.5 ± 4.5 |
| ptsH1 | 26.7 ± 6.5 | 35.3 ± 7.2 |
| ccpA | 19.4 ± 0.7 | 30.6 ± 4.3 |

$^a$ N-acetylglucosaminidase activity was determined using p-nitrophenyl-N-acetyl-β-D-glucosaminide as substrate. Activity is expressed in nmoles per min per mg of cells (dry weight)

The hprK208(Am) Mutation Affects Diauxic Growth

Growth of the hprK208(Am) mutant LcG102 in MRS medium containing 0.05% glucose and either 0.05% lactose or 0.05% maltose was compared to the growth behaviour of the wild-type strain ATCC 393. Wild-type L. casei grown in media containing mixtures of glucose and lactose or glucose and maltose exhibited a diauxic growth curve characterized by two distinct growth phases separated by a lag phase of about 8 h for cells growing on glucose/lactose and 7 h for cells growing on glucose/maltose medium. In the hprK208(Am) mutant LcG102, the lag phase was reduced to less than 3 h for cells grown in either glucose and lactose- or glucose and maltose-containing medium.

The hprK208(Am) Mutation Prevents the Exclusion of Maltose by Glucose

It is shown above that replacement of Ser-46 in *L. casei* HPr with alanine or threonine or replacement of Ile-47 with threonine prevents the exclusion of maltose by glucose. To ensure that the observed effect of the ptsH mutations is indeed due to the absence of ATP-dependent, HprK-catalyzed phosphorylation of HPr in the ptsH mutants and not due to structural changes of HPr caused by the mutations, we studied glucose-triggered maltose exclusion in the hprK208(Am) mutant strain LcG102. Maltose uptake by wild-type cells was instantaneously arrested when glucose was added to the transport medium. By contrast, when an identical experiment was carried out with the hprK208(Am) mutant LcG102, maltose uptake was not inhibited but rather slightly stimulated by the presence of glucose. The absence of glucose-triggered maltose exclusion in the hprK208(Am) mutant was confirmed by measuring maltose consumption in the presence and absence of 0.15% glucose with *L. casei* wild-type and hprK208(Am) mutant strains. In the wild-type strain, maltose was not utilized as long as glucose was present in the growth medium, whereas maltose and glucose were simultaneously consumed by the hprK208(Am) mutant LcG102.

EXAMPLE 5

Construction and Characterisation of Food-Grade ptsI and ccpA Mutants

Food grade mutants of ptsI or ccpA genes were constructed in the industrial strain of *L. paracasei* subsp. *paracasei* CNCM I-1518; this strain is disclosed in EP 0 794 707.
Construction of a ptsI Mutant
This mutant was constructed using the method of Example 2.
Plasmid pVMR10 was used to transform *L. casei* CNCM I-1518.
The transformed strain was grown in MRS medium comprising 5 µg/ml erythromycin. An erythromycin-resistant ptsI⁺ integrant was isolated. This integrant was grown for 200 generations in MRS medium without erythromycin to allow the second recombination leading to the excision of the pVMR10 plasmid.
An erythromycin-sensitive Lac⁻ clone was isolated as disclosed by Example 2 above, checked by PCR and its ptsI gene sequenced. The fermentation pattern of this clone in API-CH50L showed that, when compared to the wild type CNCM I-1518, this mutant could no longer use adonitol, fructose, mannose, sorbose, mannitol, sorbitol, amygdaline, arbutine, salicine, cellobiose, sucrose and trehalose.
This mutant was grown at 37° C. in low-fat milk (13 g fat/kg) or skim milk. In skim milk, a pH of 4.45 was reached after 34 h (under the same conditions a pH of 4.45 was reached after 30 h with the wild-type strain CNCM I-1518).
In another series of tests, standardized milk having 170 g protein/kg, 13 g fat/kg, and supplemented with 50 g glucose/kg was used.
The fermented products obtained from standardized milk supplemented with glucose with the mutant strain ptsI have a gel-strength lower of about 15-25% than the fermented products obtained from the wild-type strain. This allows to obtain a more elastic gel of about 15-25% and to reduce syneresis.
They also have a slightly lower viscosity than the fermented products obtained with the wild-type strain. However, the loss of viscosity under shearing is less important in the case of the products obtained with the mutant strain. This property allows a better conservation of the texture during industrial processes wherein shearing may occur, such as the preparation of stirred fermented milk.

The fermented products obtained with the mutant strain had a more creamy flavour than the fermented products obtained with the wild-type strain. This is related to a higher content in C4, C6, C8, C12, C14, and C16 fatty acids.
Construction of a ccpA Mutant
Mutants in *L. casei* BL23 and CNCM I-1518 were constructed with the following procedure:
Plasmid pJDC9 [CHEN and MORRISON, Gene, 64, 155-164, (1998)] carrying a SalI restriction fragment of 2.6 kb that included ccpA gene and flanking regions, was digested with EcoRI, made blunt end (filled in with the Klenow enzyme), ligated and transformed in *E. coli* DH5α. This plasmid (pJ-δccpA) was used to transform both *L. casei* strains.
The transformed strains were grown in MRS medium comprising 5 µg/ml erythromycin and erythromycin-resistant integrants were isolated.
Then, one integrant of each transformation event was grown for 200 generations in MRS medium without erythromycin leading to the excision of the plasmid. Erythromycin-sensitive colonies showing slower growth were screened by PCR amplification of ccpA, followed by digestion with EcoRI. Strains where the amplified fragment was not digested by EcoRI were further analysed by sequencing the ccpA gene. Sequencing of the ccpA mutant gene showed that an insertion of four nucleotides (AATT) had occurred at position 710 of the sequence U28137 of GENBANK. This insertion generated a stop codon 5 codons after the mutation site and resulted in a truncated CcpA protein of 143 amino acids that is inactive.
When this mutant was grown at 37° C. in skim milk, a pH of 4.45 was reached after 45 h.
The fermented products obtained with the mutant strain from standardized milk supplemented with glucose had a content in acetic acid, succinic acid, and formic acid twice higher than the fermented products obtained from the wild-type strain. They also contained the same quantity of lactate than the products obtained from the wild-type strain. They contained less citrate, due to a citrate consumption by the ccpA mutant 10 times higher than by the wild-type strain.
They had also a higher content in acetoin (4 to 6 times higher) than the fermented products obtained from the wild-type strain.
The overproduction of acetoin by the ccpA mutant indicates that it is potentially able to overproduce diacetyl under appropriate conditions (i.e. oxidative conditions which promotes the conversion of α-acetolactate into diacetyl rather than into acetoin).

EXAMPLE 6

Post-Acidification Properties of Food Grade ptsI and ccpA Mutants

Figure 7:
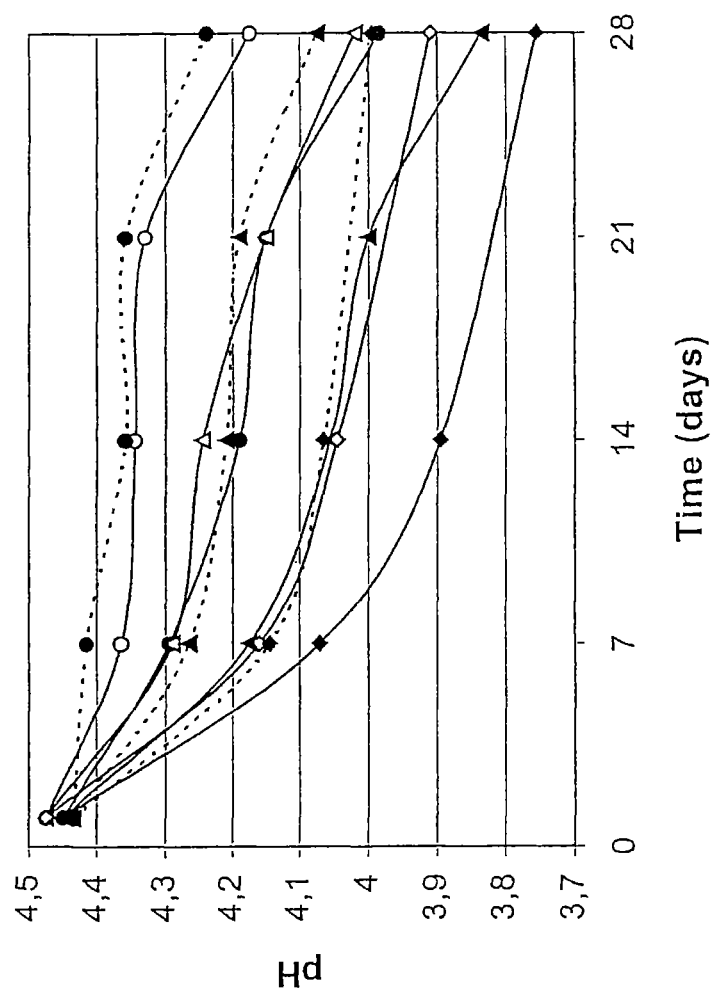
FIG. 7: represents the post-acidification during storage at different temperatures for fermented milks obtained with the wild-type strain or with the ccpA or ptsI mutant.

The ptsI and ccpA mutants of Example 5 were grown as described above on standardized milk supplemented with glucose until a pH of about 4.55.
The fermented milks thus obtained are stored at 4° C., 8° C., or 13° C., and the pH is measured after 7, 14, 21, or 28 days of storage.
FIG. 7 represents the post-acidification during storage at different temperatures for fermented milks obtained with the wild-type strain or with the ccpA or ptsI mutant.
Legend of FIG. 7:
—●—: wild type strain 4° C.:
—▲—: wild type strain 8° C.
—◆—: wild type strain 13° C.
—○—: ccpA mutant 4° C.

—△—: ccpA mutant 8° C.
—◇—: ccpA mutant 13° C.
—●—: ptsI mutant 4° C.
—▲—: ptsI mutant 8° C.
—◆—: ptsI mutant 13° C.

These results show that in every case, the ccpA and ptsI mutants have a reduced post-acidification compared with the wild-type strain.

This reduced post-acidification is not due to a lower survival of the mutant strains. This was controlled by measuring the survival rate at 28 days. It is higher than 60% for the ccpA and ptsI mutants as well as for the wild-type strain.

The invention claimed is:

1. A method for preparing a food product or food additive, wherein said method comprises fermenting a food substrate with a mutant of *L. casei* having at least one mutation in the ptsI gene, wherein said mutation impairs the regulation of carbon catabolite repression mechanisms.

2. A method of claim 1, wherein said food product is a dairy product.

3. A method for preparing a food product, comprising fermenting a food substrate with a mutant of *L. casei* having a mutation impairing the function of enzyme I encoded by the ptsI gene.

4. A fermented food product obtainable by a method according to claim 1.

5. A fermented food product comprising at least a mutant of *L. casei* having at least one mutation in the ptsI gene, wherein said mutation impairs the regulation of carbon catabolite repression mechanisms.

6. A fermented food product obtainable by the method according to claim 3.

7. A fermented food product according to claim 6, comprising at least a mutant strain of *L. casei* as defined in claim 3.

* * * * *